United States Patent [19]
Miller et al.

[11] Patent Number: 6,019,957
[45] Date of Patent: Feb. 1, 2000

[54] NON-STEROIDAL RADIOLABELED AGONIST/ANTAGONIST COMPOUNDS AND THEIR USE IN PROSTATE CANCER IMAGING

[75] Inventors: Duane D. Miller, Germantown; Leonid I. Kirkovsky, Memphis; James T. Dalton, Memphis; Arnab Mukherjee, Memphis, all of Tenn.

[73] Assignee: The University of Tennessee Research Corporation, Knoxville, Tenn.

[21] Appl. No.: 09/090,425

[22] Filed: Jun. 4, 1998

Related U.S. Application Data

[60] Provisional application No. 60/049,376, Jun. 4, 1997.

[51] Int. Cl.[7] .................................................. A61K 51/00
[52] U.S. Cl. ...................... 424/1.65; 424/1.85; 424/1.89; 548/231; 558/413; 558/414; 564/162; 564/170; 564/202
[58] Field of Search ........................... 548/231; 558/413, 558/414; 564/162, 170, 202; 424/1.65, 1.85, 1.89

[56] References Cited

U.S. PATENT DOCUMENTS

| | | | |
|---|---|---|---|
| 3,875,229 | 4/1975 | Gold | 564/202 |
| 4,139,638 | 2/1979 | Neri et al. | 514/624 |
| 4,191,775 | 3/1980 | Glen | 558/414 X |
| 4,239,776 | 12/1980 | Glen et al. | 558/414 X |
| 4,282,218 | 8/1981 | Glen et al. | 514/178 |
| 4,386,080 | 5/1983 | Crossley et al. | 558/413 X |
| 4,465,507 | 8/1984 | Konno et al. | 558/413 X |
| 4,636,505 | 1/1987 | Tucker | 564/202 X |
| 4,880,839 | 11/1989 | Tucker | 564/170 X |
| 4,977,288 | 12/1990 | Kassis et al. | 556/87 |

FOREIGN PATENT DOCUMENTS

| | | |
|---|---|---|
| 0002892 A1 | 12/1978 | European Pat. Off. . |
| 0040932 A1 | 5/1981 | European Pat. Off. . |
| 0100172 A1 | 7/1983 | European Pat. Off. . |
| 52-128329 | 10/1977 | Japan . |
| 54-63047 | 5/1979 | Japan . |
| 1360001 | 3/1970 | United Kingdom . |
| 95-19770 | 7/1995 | WIPO . |

OTHER PUBLICATIONS

Kirkovsky et al., "Approaches to Irreversible Non–Steroidal Chiral Antiandrogens," 47th Southeast/51st Southwest Joint Regional Meeting of the American Chemical Society, Memphis, TN (Nov. 29–Dec. 1, 1995).

McKillop et al., "Enantioselective Metabolism and Pharmacokinetics of Casodex in the Male Rat," Xenobiotica, 25(6):623–634 (1995).

Tucker et al., "Resolution of the Nonsteriodal Antiandrogen 4'–Cyano–3–[4–fluorophenyl) sulfonyl]–2–hydroxy–2–methyl–3'–(trifluoromethyl)–propionanilide and the Determination of the Absolute Configuration of the Active Enantiomer," *J. Med. Chem.*, 31(4):885–887 (1988).

Berger et al., "Concepts and Limitations in the Application of Radiolabeled Antiandrogens, Estrogens, or Androgens as Isotopic Scanning Agents for the Prostate", Invest. Urol, (1975), 1391, 10–16.

*Primary Examiner*—Fiona T. Powers
*Attorney, Agent, or Firm*—Nixon Peabody LLP

[57] ABSTRACT

The present invention relates to a radiolabeled non-steroidal compound having the formula:

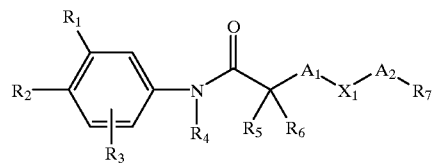

where $R_1$, $R_2$, and $R_3$, are the same or different and are a radioactive or nonradioactive halogen, a nitro, a cyano, a carbamoyl, a hydrogen, a perfluoroalkyl, a haloalkylamido, an isothiocyanate, an azide, a diazocarbonyl, a substituted oxirane, or a β-chloroethylamine;

$R_4$ is a hydrogen, an alkyl, or is joined to $R_5$;

$R_5$ is a radioactive or nonradioactive halogen, a hydrogen, a hydroxy, an alkyl, a haloalkyl, an alkoxy, an acyloxy, an amino, an alkylamino, a thio, a thioalkyl, or is joined to $R_4$;

$R_6$ is a hydrogen, an alkyl, a halogen, or a haloalkyl;

$A_1$ and $A_2$ are the same or different, and each is a direct link or an alkylene;

$X_1$ is a radioactive or nonradioactive halogen, an oxygen, a sulfur, a sulphinyl, a sulphonyl, an amino, an alkylimino, or alkylene;

$R_7$ is a radioactive or nonradioactive halogen, a hydrogen, an alkoxy, a haloalkoxy, an acyloxy, a haloacyloxy, an aryloxy, a thioalkyl, a thioraryl, an alkylsulphinyl, an arylsulphinyl, an alkylsulphonyl, an arylsulphonyl, an amino, an alkylimino, an alkylamido group, a radioactive or nonradioactive haloalkylamido group, a phenyl optionally substituted with a radioactive or nonradioactive halogen, a nitro group, an alkyl, a radioactive or nonradioactive haloalkyl, a cyano, a hydroxyl, a carboxyl group, an amino, an alkylamino group, a dialkylamino group, a bisalkylamino group, a radioactive or nonradioactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradioactive bis(haloacyl) imido group, or a radioactive or nonradioactive alkylhaloacylamido group.

19 Claims, 3 Drawing Sheets

NON-STEROIDAL RADIOLABELED AGONIST/ANTAGONIST COMPOUNDS AND THEIR USE IN PROSTATE CANCER IMAGING

This application claims the benefit of U.S. Provisional Patent Application Ser. No. 60/049,376, filed Jun. 4, 1997, which is hereby incorporated by reference.

FIELD OF THE INVENTION

The present invention relates to non-steroidal radiolabeled androgen receptor ligands and their use in imaging of prostate cancer.

BACKGROUND OF THE INVENTION

Throughout this application, various publications are referenced, many in parenthesis. The disclosures of these publications in their entireties are hereby incorporated by reference in this application.

Androgens are known to stimulate growth of the prostate and other peripheral tissues, including primary or metastatic prostate tumor cells. Testosterone ("T") is the principal androgen secreted by the testes and is the primary circulating androgen found in the plasma of males. The testes produce 95% of circulating plasma T, while the remaining 5% is derived from the adrenals. In many target tissues, T is converted by the enzyme 5α-reductase to the more potent androgen dihydrotestosterone ("DHT"). T and DHT then compete for binding to the androgen receptor ("AR") to exert their influence on cell function. DHT has a four- to five-fold higher AR binding affinity than does T and thus serves as the intracellular mediator for most actions of the hormone. However, both androgens contribute to the overall androgenic effect. The high response rate (i.e., 60 to 80%) to first line hormonal therapy and the presence of AR in both primary and metastatic prostate tumor cells support the idea that the AR is an important mediator of prostate cancer development and growth (Denis et al., "Prostatic Cancer: An Overview," *Acta. Oncol.*, 29:665–77 (1990) ("Denis"); McConnell, "Physiologic Basis of Endocrine Therapy for Prostatic Cancer," *Urol. Clin. N. Am.*, 18(1):1–13 (1991)).

Prostate cancer is the most frequently diagnosed non-skin cancer in American men, accounting for approximately 27% of all cancer cases (Boring, *Cancer Statistics* 43:7–26 (1993)). Treatment for prostate cancer depends on the stage at which the cancer is found, and on the age and health status of the patient. As with other malignancies, accurate staging of prostate cancer is absolutely critical in selecting the most appropriate form of therapy. Clinically localized disease is potentially curable with standard surgery and/or radiation therapy. However, no curative therapies exist for advanced disease. Existing diagnostic tests such as magnetic resonance imaging ("MRI"), computed tomographic scans ("CT"), and ultrasound ("US") lack both the specificity and sensitivity to substitute for exploratory surgery in staging malignant disease. Because of inadequate diagnostic studies, patients with what is presumed to be surgically curable prostate cancer must submit to surgical staging to determine the presence or absence of lymph node metastases. Almost half of the men initially diagnosed with local disease are found to have tumors which have advanced to the periprostatic area or beyond at the time of surgery (Carter et al., In: "A Multidisciplinary Analysis of Controversies in the Management of Prostate Cancer," Coffey et al., eds., pp. 1–7, Plenum, New York). Thus, nearly one-third of all men diagnosed with prostate cancer (i.e., about 80,000 men per year) undergo surgery from which they are unlikely to benefit. Thus, non-invasive, more selective, and more accurate imaging tools for prostate cancer are needed.

Knowledge of the presence, location, and extent of disease aids in selecting which patients are likely to benefit from radical surgery, radiotherapy, or androgen ablation. Single photon emission computed tomography ("SPECT") is a form of chemical imaging in which emissions from radiopharmaceuticals, labeled with gamma-emitting radionuclides (e.g. $^{99m}$Tc, $^{67}$Ga, $^{111}$In, or $^{123}$I) are used to create cross-sectional CT images of radioactivity distribution in vivo. Imaging of this type is typically done with non-specific compounds (e.g. albumin or chelating agents like DTPA) complexed with the radionuclide. This, and similar methods, thus have the potential to improve the ability of CT and MRI to detect lymph nodes as well as bony and other visceral metastases. However, these methods are not selective. Radioimmunoscintigraphy using monoclonal antibodies ("MoAbs") which recognize prostate-specific proteins, including PSA and prostatic acid phosphatase ("PAP"), was developed as a means to specifically image the tumor, as opposed to the underlying host tissues. This approach has met with some success for these purposes (Dillman et al., "Radioimmunodetection of Cancer With The Use of Indium-111-Labeled Monoclonal Antibodies," *Natl. Cancer Inst. Monogr.*, 3:33 (1987); Vihko et al., "Immunoscintigraphic Evaluation of Lymph Node Involvement in Prostate Carcinoma," *Prostate* 11:51 (1987)). Prostascint is an IgG1 murine monoclonal antibody conjugated to the $^{111}$In chelator GYK-DTPA to form the immunoconjugate $^{111}$In capromab pendetide. This antibody conjugate is reported to have a high degree of binding to all prostate cancers and mild binding to benign prostatic hypertrophic and normal prostate tissue. Preliminary data showed that this MoAb was able to detect disease foci of 5 mm or greater with a negative predictive value of 83% and positive predictive value of 50%, suggesting that radioimaging is a promising technique for prognostication of prostate cancer (Babaian et al., "Radioimmunoscintigraphy of Pelvic Lymph Nodes With 111-Indium-Labeled Monoclonal Antibody CYT-356," *J. Urol.*, 152:1952 (1994)). However, a major concern is that patients may develop human antimurine antibody ("HAMA") responses as a result of the murine origin of the antibody, resulting in adverse reactions and precluding the use of subsequent antibody imaging (Babaian et al., "Radio-immunological Imaging of Metastatic Prostate Cancer With 111-Indium-Labeled Monoclonal Antibody PAY276," *J. Urol.*, 137:439 (1987)).

Chemical imaging represents a viable alternative to immunological methods. In this instance, the increase in imaging specificity is gained as the result of the preferential distribution of a radiochemical into an anatomical region of interest. Wolf recently defined pharmacokinetic imaging as the measurement of the rate of change of a radiochemical in an anatomic space, or chemical imaging with the added dimension of time (Wolf, "Imaging Can Be Much More Than Pretty Pictures," *Pharmaceut. Res.*, 12:1821–22 (1995)). This technique can be powerful, because it allows one to obtain noninvasive measurements of the pharmacokinetics and pharmacodynamics of a radiolabeled compound at the target tissue site (Presant et al., "Association of Intratumoral Pharmacokinetics of Fluorouracil With Clinical Response," *The Lancet*, 343:1184–87 (1994); Dowell et al., "Pharmacokinetic Parameters of Cisplatin Can Be Estimated in Human Tumors by Noninvasive Measurements of the Biodistribution and Targeting of $^{195m}$Pt cisplatin," *Proc. Am. Assoc. Cancer Res.*, 36:360 (1995)). Receptor-mediated chemical imaging has been used for the imaging of other endocrine tumors. [111]In pentetreotide (Octreoscan®) is used clinically for the imaging of somatostatin receptors present in neuroendocrine tumors. It has also been shown that 16α-[$^{18}$F]fluoroestradiol and 21-[$^{18}$F]fluoro-16α-ethyl-19-norprogesterone can be used with positron emission tomography ("PET") to provide clear images of both estrogen and progesterone receptor-positive breast tumors (Mintun et al., "Positron Tomographic Imaging of Estrogen Receptors in Human Breast Tumors," *Radiology*, 169:45 (1988); McGuire et al., "Positron Tomographic Assessment of 16α-[$^{18}$F]-Fluoroestradiol Uptake in Metastatic Breast Carcinoma," *J. Nucl. Med.*, 32:1526 (1991); Pomper et al., "21-[$^{18}$F]fluoro-16α-ethyl-19-norprogesterone: Synthesis and Target Tissue Selective Uptake of a Progestin Receptor Based Radiotracer for Positron Emission Tomography," *J. Med. Chem.*, 31:1360 (1988); Dehdashti et al., "Assessment of 21-[$^{18}$F]fluoro-16α-ethyl-19-norprogesterone as a Positron-Emitting Radiopharmaceutical for Detection of Progestin Receptors in Human Breast Carcinomas," *J. Nucl. Med.*, 32:1532 (1991)). A variety of steroidal androgens incorporating photon-emitting and positron-emitting radionuclides have been synthesized and evaluated for their potential in imaging AR-positive tumors of the prostate (Carlson et al., "A Comparative Study of the Selectivity and Efficiency of Target Tissue Uptake of Five Tritium-labeled Androgens in the Rat," *J. Steroid Biochem.*, 36:549 (1990) ("Carlson"); Brandes et al., "Fluorinated Androgens and Progestins: Molecular Probes for Androgen and Progesterone Receptors with Potential Use in Positron Emission Tomography," *Molec. Pharmacol.*, 32:391 (1987) ("Brandes"); Liu et al., "20-[$^{18}$F]fluoro-mibolerone, A Positron-Emitting Radiotracer For Androgen Receptors: Synthesis and Tissue Distribution Studies," *J. Nucl. Med.*, 32:81 (1991) ("Liu 1991"); Choe et al., "Synthesis of 11β-[$^{18}$F]fluoro-5α-dihydrotestosterone and 11β[-$^{18}$F] fluoro-19-nor-5α-dihydrotestosterone: Preparation Via Halofluorination-Reduction, Receptor Binding, and Tissue Distribution," *J. Med. Chem.*, 38:816 (1995) ("Choe"); Liu et al., "Synthesis of High Affinity Fluorine-Substituted Ligands for the Androgen Receptor. Potential Agents for Imaging Prostatic Cancer By Positron Emission Tomography," *J. Med. Chem.*, 35:2113 (1992) ("Liu 1992"); Hoyte et al., "7α-methyl-17α-(E-2'-[$^{125}$I]iodovinyl)-19-nortestosterone: A New Radioligand for the Detection of Androgen Receptor," *Steroids* 58:13 (1993) ("Hoyte"); Ali et al., "Synthesis of 17α, 20E/Z)iodovinyl testosterone and 19-nortestosterone Derivatives as Potential Radioligands for Androgen and Progesterone Receptors," *J. Steroid Biochem. Mol. Biol.*, 49:15 (1994) ("Ali")). However, the majority of these compounds were not useful for AR-mediated imaging due to rapid metabolic cleavage of the radiolabel, low AR binding affinity, or inadequate specific activity. Carlson and Katzenellenbogen examined the target tissue selectivity of tritiated testosterone, dihydrotestosterone, 19-nortestosterone, mibolerone (MIB), and methyltrienolone (R1881) in rats, concluding that compounds with AR binding affinities comparable to or greater than that of testosterone would be required to provide adequate target tissue uptake and target to non-target contrast for successful in vivo imaging of androgen target tissues (Carlson). MIB and R 1881 demonstrated encouraging selectivity and target tissue uptake in animal models, most likely due to their slower in vivo metabolic clearance as compared to the other androgens (Carlson; Brandes; Liu 1992; Choe; Liu 1991). Bonasera ("Preclinical Evaluation of fluorine-18-labeled Androgen Receptor Ligands in Baboons," *J. Nucl. Med.*, 37:1009–15 (1996)) studied $^{18}$F-labeled steroids using PET in baboons and is now studying 16β-[$^{18}$F]fluoro-5α-dihydrotestosterone in men with metastatic prostate cancer.

Based on previous reports, the most important properties of radiolabeled androgens with respect to AR imaging appear to be: (i) the selectivity and affinity for AR binding; and (ii) the rate of in vivo metabolism (Carlson; Brandes; Liu 1992; Choe; Liu 1991; Hoyte; Ali). Androgenic steroids, like other steroids, are known to bind with other steroid receptors (Carlson; Dunn et al., "Transport of Steroid Hormones: Binding of 21 Endogenous Steroids to Both Testosterone-binding Globulin and Corticosteroid-binding Globulin in Human Plasma," *J. Clin. Endrocrinol.*, 53:58 (1981) ("Dunn")). Binding of steroidal AR-imaging agents to progesterone and/or glucocorticoid receptors in the body contributes to their poor target site specificity for imaging. Radioactivity levels that remain in the blood or in non-target tissues are affected by the extent to which the agent binds to high affinity, non-target proteins (Carlson; Choe; Ali). Further, the natural androgens (i.e., testosterone and dihydrotestosterone) are extensively bound to sex hormone-binding globulin ("SHBG"), a high affinity, low capacity binding plasma protein (Dunn). Not surprisingly, many of the synthetic androgens also bind to SHBG with high affinity (Carlson; Brandes; Liu 1991; Liu 1992; Choe; Hoyte; Ali). These high affinity SHBG sites compete with the AR for specific binding of the radiolabeled ligand, and have precluded the use of a number of steroidal AR ligands for imaging. The metabolic fate and pharmacokinetics of AR-imaging agents are also important factors determining their usefulness for in vivo imaging (Carlson). Studies with estrogen and progestin imaging agents showed that in vivo target to nontarget uptake ratios correlated with the ratio of specific to non-specific binding in vitro (vanBrocklin et al., "16β-([$^{18}$F]fluoro)estrogens: Systematic Investigation of a New Series of Fluorine-18-Labeled Estrogens as Potential Imaging Agents for Estrogen-Receptor-Positive Breast Tumors," *J. Med. Chem.*, 35:1619 (1993)). However, it was recently found that this relationship did not hold for a series of androgen analogs (Choe). In the series of compounds therein, the compound with highest relative binding affinity ("RBA") and lowest non-specific binding had a poor target to nontarget tissue uptake ratio, while the compound with the lowest RBA demonstrated the highest target to nontarget tissue ratio in vivo. As a whole, these data strongly suggest that in vivo metabolism is a major factor in determining the distribution profile in vivo (Carlson; Brandes; Choe; Ali).

The present invention is directed to overcoming these deficiencies.

SUMMARY OF THE INVENTION

The present invention relates to a radiolabeled non-steroidal compound having the formula:

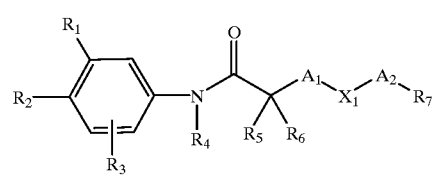

where
R$_1$, R$_2$ and R$_3$, are the same or different and are a radioactive or nonradioactive halogen, a nitro, a cyano, a carbamoyl, a hydrogen, a perfluoroalkyl, a haloalkylamido, an isothiocyanate, an azide, a diazocarbonyl, a substituted oxirane, or a β-chloroethylamine;

$R_4$ is a hydrogen, an alkyl, or is joined to $R_5$;

$R_5$ is a radioactive or nonradioactive halogen, a hydrogen, a hydroxy, an alkyl, a haloalkyl, an alkoxy, an acyloxy, an amino, an alkylamino, a thio, a thioalkyl, or is joined to $R_4$;

$R_6$ is a hydrogen, an alkyl, a halogen, or a haloalkyl;

$A_1$ and $A_2$ are the same or different, and each is a direct link or an alkylene;

$X_1$ is a radioactive or nonradioactive halogen, an oxygen, a sulfur, a sulphinyl, a sulphonyl, an amino, an alkylimino, or an alkylene;

$R_7$ is a radioactive or nonradioactive halogen, a hydrogen, an alkoxy, a haloalkoxy, an acyloxy, a haloacyloxy, an aryloxy, a thioalkyl, a thioraryl, an alkylsulphinyl, an arylsulphinyl, an alkylsulphonyl, an arylsulphonyl, an amino, an alkylimino, an alkylamido group, a radioactive or nonradioactive haloalkylamido group, or a phenyl optionally substituted with a radioactive or nonradioactive halogen, a nitro group, an alkyl, a radioactive or nonradioactive haloalkyl, a cyano, a hydroxyl, a carboxyl group, an amino, an alkylamino group, a dialkylamino group, a bisalkylamino group, a radioactive or nonradioactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradioactive bis(haloacyl)imido group, or a radioactive or nonradioactive alkylhaloacylamido group.

The present invention also relates to a pharmaceutical composition which includes a compound and a pharmaceutically suitable carrier.

The present invention further relates to a method of imaging for prostate cancer in a patient which includes contacting an androgen receptor with a radiolabeled non-steroidal compound under conditions effective to bind the radiolabeled non-steroidal compound to the androgen receptor of the patient and detecting the presence of any radiolabeled non-steroidal compound bound to the androgen receptor.

The present invention also relates to a precursor compound having the formula as shown above, wherein $R_1$, $R_2$, and $R_3$ are the same or different, and each is a hydrogen, a halogen, a nitro, a cyano, a carbamoyl, a perfluoroalkyl, a haloalkylamido, an isothiocyanate, an azide, a diazocarbonyl, a substituted oxirane, a β-chloroethylamine, a diazonium salt, a triazene group, a tertiary alklyl group, an oxy group, an alkoxy group, a stannoalkyl group, a stannoaryl group, an unsubstituted or substituted boronic acid, an alkyl silane group, a pentaflourosilicate group, an alkylgermano group, a halomercury group, a trifluoroacetylthallate group, a thallium difluoride group, or other defined substituents;

$R_4$ is a hydrogen, an alkyl, or is joined to $R_5$;

$R_5$ is a hydrogen, a hydroxy, an alkyl, a haloalkyl, an alkoxy, an acyloxy, an amino, an alkylamino, a thiol, a thioalkyl, a halogen, or is joined to $R_4$ or $X_1$;

$R_6$ is a hydrogen, an alkyl, a halogen, or a haloalkyl;

$A_1$ and $A_2$ are the same or different, and each is a direct link or alkylene;

$X_1$ is a halogen, an oxygen, a sulfur, a sulphinyl, a sulfonyl, an amino, or an alkylimino, an alkylene, or is joined to $R_5$ directly, through an oxirane ring, through an $SO_2$ group, or through an SO group;

$R_7$ is an aryl ring, substituted at different positions with a hydrogen, a halogen, a diazonium salt, a triazene group, a tertiary alkyl amino group, a nitro group, an oxy or an alkoxy group, an amino or an alkylamino group, a stannoalkyl group, a stannoaryl group, an unsubstituted or a substituted boronic acid, an alkyl silane group, a pentafluorosilicate group, an alkylgermano group, a halomercury group, a trifluoroacetyl thallate group, or a thallium difluoride group.

Another aspect of the present invention relates to a method of producing the radiolabeled non-steroidal compound which includes providing the precursor compound, providing a radioactive compound, and reacting the precursor compound with the radioactive compound under conditions effective to produce the radiolabeled non-steroidal compound.

The compounds of the present invention have an AR binding affinity several-fold greater than other nonsteriodal AR ligands and, accordingly, will bind and be retained to the AR in primary and metastatic tumor cells. As such, they are useful in imaging of prostate cancer and other tissues containing androgen receptors.

DETAILED DESCRIPTION OF THE INVENTION

Figure 1:
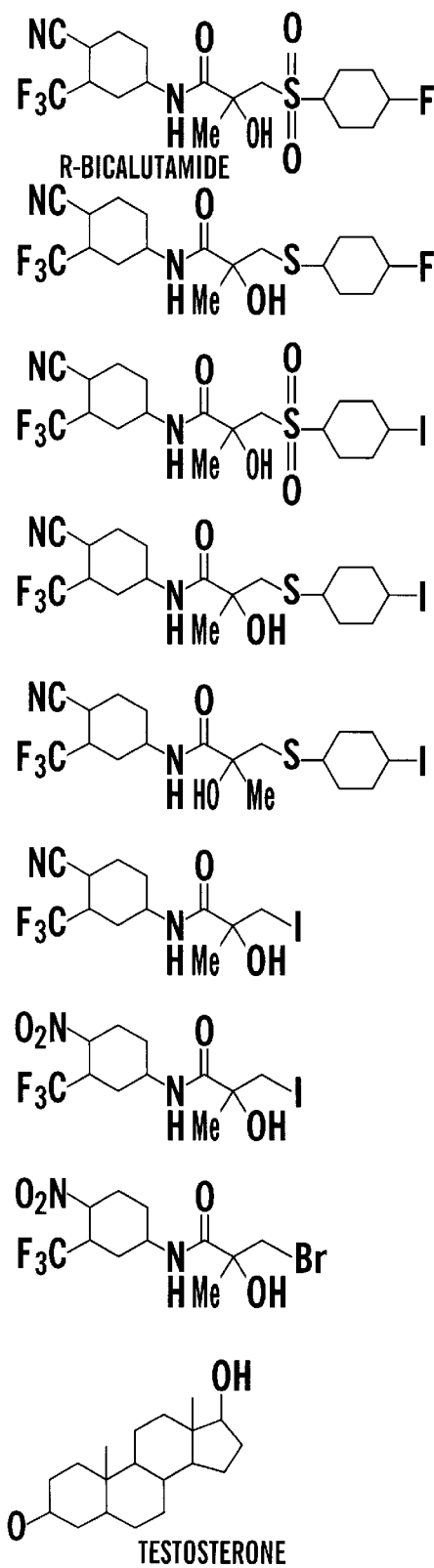
FIG. 1 is a bar graph that shows the binding affinities of compounds of the present invention to AR.
Figure 1:
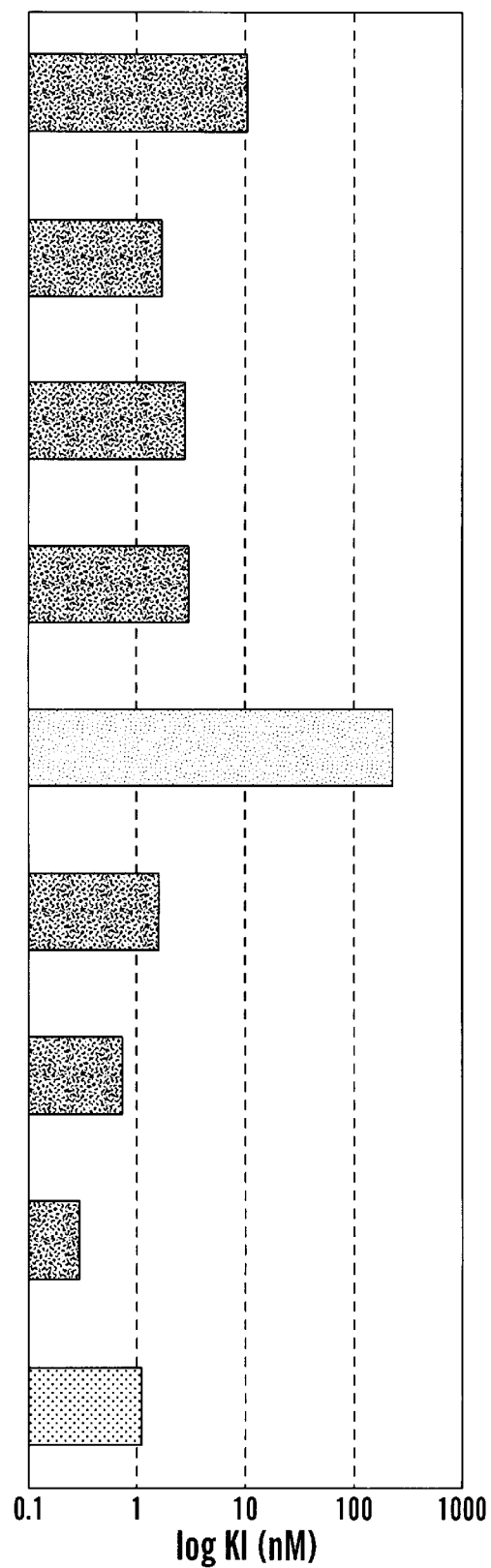

The present invention relates to a radiolabeled non-steroidal compound having the formula:

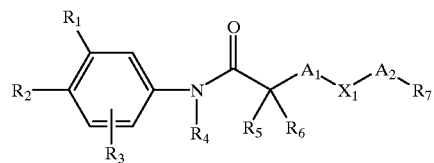

where $R_1$, $R_2$, and $R_3$ are the same or different and are a radioactive or nonradioactive halogen, a nitro, a cyano, a carbamoyl, a hydrogen, a perfluoroalkyl, or a haloalkylamido;

$R_4$ is a hydrogen, an alkyl, or is joined to $R_5$;

$R_5$ is a radioactive or nonradioactive halogen, a hydrogen, a hydroxy, an alkyl, a haloalkyl, an alkoxy, an acyloxy, an amino, an alkylamino, a thio, a thioalkyl, or is joined to $R_4$;

$R_6$ is a hydrogen, an alkyl, a halogen or a haloalkyl;

$A_1$ and $A_2$ is the same or different, each is direct link or an alkylene;

$X_1$ is a radioactive or nonradioactive halogen, an oxygen, a sulfur, a sulphinyl, a sulphonyl, an amino, an alkylimino, or an alkylene;

$R_7$ is a radioactive or nonradioactive halogen, a hydrogen, an alkoxy, a haloalkoxy, a acyloxy, a haloacyloxy, an aryloxy, a thioalkyl, a thioraryl, an alkylsulphinyl, an arylsulphinyl, an alkylsulphonyl, an arylsulphonyl, an amino, an alkylimino, an alkylamido group, a radioactive or nonradioactive haloalkylamido group, or a phenyl optionally substituted with a radioactive or nonradioactive halogen, a nitro group, an alkyl, a radioactive or nonradioactive haloalkyl, a cyano, a hydroxyl, a carboxyl group, an amino, an alkylamino group, a dialkylamino group, a bisalkylamino group, a radioactive or nonradioactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradioactive bis(haloacyl)imido group, or a radioactive or nonradioactive alkylhaloacylamido group. The compound binds to an androgen receptor.

The subject invention is best understood through a discussion of receptors and signal transduction pathways. Cells in higher animals normally communicate by means of hundreds of kinds of extracellular signaling molecules, including proteins, small peptides, amino acids, nucleotides, steroids, retinoids, fatty acid derivatives, and even dissolved gases such as nitric oxide and carbon monoxide. These signaling molecules relay a "signal" to another cell (a "target cell"), generally affecting a cellular function. As used herein, receptors for extracellular signaling molecules are collectively referred to as "cell signaling receptors".

Many cell signaling receptors are transmembrane proteins on a cell surface; when they bind an extracellular signaling molecule (a ligand), they become activated so as to generate a cascade of intracellular signals that alter the behavior of the cell. In contrast, in some cases, the receptors are inside the cell and the signaling ligand has to enter the cell to activate them; these signaling molecules therefore must be sufficiently small and hydrophobic to diffuse across the plasma membrane of the cell. As used herein, these receptors are collectively referred to as "intracellular cell signaling receptors".

Steroid hormones are one example of small hydrophobic molecules that diffuse directly across the plasma membrane of target cells and bind to intracellular cell signaling receptors. These receptors are structurally related and constitute the intracellular receptor superfamily (or steroid-hormone receptor superfamily). Steroid hormone receptors include progesterone receptors, estrogen receptors, androgen receptors, glucocorticoid receptors, and mineralocorticoid receptors. The present invention is particularly directed to androgen receptors.

In addition to ligand binding to the receptors, the receptors can be blocked to prevent ligand binding. When a substance binds to a receptor, the three-dimensional structure of the substance fits into a space created by the three-dimensional structure of the receptor in a ball and socket configuration. The better the ball fits into the socket, the more tightly it is held. This phenomenon is called affinity. If the affinity of a substance is greater than the original hormone, it will compete with the hormone and bind the binding site more frequently. Once bound, signals may be sent through the receptor into the cells, causing the cell to respond in some fashion. This is called activation. On activation, the activated receptor then directly regulates the transcription of specific genes. But the substance and the receptor may have certain attributes, other than affinity, in order to activate the cell. Chemical bonds between atoms of the substance and the atoms of the receptors must form. In some cases, this leads to a slight change in the configuration of the receptor which is enough to begin the activation process (called signal transduction). As a result, substances can be made which bind receptors and activate them (called receptor agonists) or inactivate them (called receptor antagonists).

The present invention is directed to compounds which are labeled antagonist or agonist compounds. Preferably, the compound of the present invention is a labeled non-steroidal ligand which binds the androgen receptor. Although it is preferable for the compounds to be antagonists, and, therefore, to inactivate the androgen receptor, labeled agonist compounds may be used if desired.

The radiolabeled non-steroidal compounds of the present invention, which are useful in binding to the androgen receptor, are acylanilides having the formula:

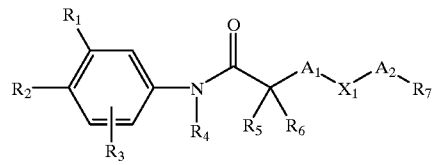

wherein $R_1$, $R_2$, and $R_3$ are the same or different, and each is a radioactive or nonradioactive halogen, a nitro, a cyano, a carbamoyl, a hydrogen, a perfluoroalkyl, a haloalkylamido, an isothiocyanate, an azide, a diazocarbonyl, a substituted oxirane, or a β-chloroethylamine;

$R_4$ is a hydrogen, an alkyl, or is joined to $R_5$;

$R_5$ is a radioactive or nonradioactive halogen, a hydrogen, a hydroxy, an alkyl, a haloalkyl, an alkoxy, an acyloxy, an amino, an alkylamino, a thio, a thioalkyl, or is joined to $R_4$;

$R_6$ is a hydrogen, an alkyl, a halogen, or a haloalkyl;

$A_1$ and $A_2$ are the same or different, and each is a direct link or an alkylene;

$X_1$ is a radioactive or nonradioactive halogen, an oxygen, a sulfur, a sulphinyl, a sulphonyl, an amino, an alkylimino, or an alkylene; and $R_7$ is a radioactive or nonradioactive halogen, a hydrogen, an alkoxy, a haloalkoxy, an acyloxy, a haloacyloxy, an aryloxy, a thioalkyl, a thioraryl, an alkylsulphinyl, an arylsulphinyl, an alkylsulphony, an arylsulphonyl, an amino, an alkylimino, an alkylamido group, a radioactive or nonradioactive haloalkylamido group, or a phenyl optionally substituted with a radioactive or nonradioactive halogen, a nitro group, an alkyl, a radioactive or nonradioactive haloalkyl, a cyano, a hydroxyl, a carboxyl group, an amino, an alkylamino group, a dialkylamino group, a bisalkylamino group, a radioactive or nonradioactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradioactive bis(haloacyl)imido group, or a radioactive or nonradioactive alkylhaloacylamido group.

Compounds of the present invention may have affinity labels at either the $R_7$ or $R_2$ position, although compounds having the affinity label at other positions may also be utilized.

A more preferred class of compounds have the above formula, wherein $R_1$ is $CF_3$, $R_2$ is CN or $NO_2$, $R_3$ is H, $R_4$ is H and $R_5$ is OH, or $R_4$ and $R_5$ are joined together as CSO, CSN, CSS, or CSC, $R_6$ is $CH_3$ or $CF_3$, $A_1$ is an alkylene or a direct link, $A_2$ is a direct link, $X_1$ is $CH_2$, S, or $SO_2$, and $R_7$ is a radioactive or nonradioactive halogen, or a phenyl optionally substituted with a radioactive or nonradioactive halogen, a nitro group, an alkyl, a radioactive or nonradioactive haloalkyl, a cyano, a hydroxyl, a carboxyl group, an amino, an alkylamino group, a dialkylamino group, a bis-alkylamino group, a radioactive or nonradioactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradioactive bis(haloacyl)imido group, or a radioactive or nonradioactive alkylhaloacylamido group.

In particular, preferred compounds of the present invention are as shown below in Tables 1 and 2.

TABLE 1

| Compound | R-isomer Compound No. | S-isomer Compound No. |
|---|---|---|
| (structure) | R-1 | S-1 |
| (structure) | R-2 | S-2 |
| (structure) | R-3 | S-3 |
| (structure) | R-4 | S-4 |
| (structure) | R-5 | S-5 | where Me is a methyl or trifluoromethyl group and I is radiolabeled (e.g., $^{125}I$ or $^{123}I$).

TABLE 2

| Isotope | Compound | Compound | Isotope |
|---|---|---|---|
| ³H | NC-C₆H₃(CF₃)-NH-C(=O)-C(Me)(OH)-CH₂-S-C₆H₃(F)(³H) | NC-C₆H₃(CF₃)-NH-C(=O)-C(Me)(OH)-CH₂-S-C₆H₄(¹⁸F) | ¹⁸F |
| ³H | NC-C₆H₃(CF₃)-NH-C(=O)-C(Me)(OH)-CH₂-S(O)₂-C₆H₃(F)(³H) | NC-C₆H₃(CF₃)-NH-C(=O)-C(Me)(OH)-CH₂-S(O)₂-C₆H₄(¹⁸F) | ¹⁸F |
| ¹²⁵I | NC-C₆H₃(CF₃)-NH-C(=O)-C(Me)(OH)-CH₂-S(O)₂-C₆H₄(¹²⁵I) | NC-C₆H₃(CF₃)-NH-C(=O)-C(Me)(OH)-CH₂-S(O)₂-C₆H₄(¹²³I) | ¹²³I |
| ¹²⁵I | NC-C₆H₃(CF₃)-NH-C(=O)-C(Me)(OH)-CH₂-S-C₆H₄(¹²⁵I) | NC-C₆H₃(CF₃)-NH-C(=O)-C(Me)(OH)-CH₂-S-C₆H₄(¹²³I) | ¹²³I |
| ¹²⁵I | O₂N-C₆H₃(CF₃)-NH-C(=O)-C(Me)(OH)-CH₂-¹²⁵I | O₂N-C₆H₃(CF₃)-NH-C(=O)-C(Me)(OH)-CH₂-¹²³I | ¹²³I |
| ¹²⁵I | NC-C₆H₃(CF₃)-NH-C(=O)-C(Me)(OH)-CH₂-¹²⁵I | NC-C₆H₃(CF₃)-NH-C(=O)-C(Me)(OH)-CH₂-¹²³I | ¹²³I | where Me is a methyl or trifluoromethyl group.

The high response rate to first line hormonal therapy and the presence of AR in both primary and metastatic prostate tumor cells support the idea that AR is an important mediator of prostate cancer development and growth. Accordingly, by binding the compound of the present invention to the AR of a patient, therefore, the accurate imaging of prostate tumors can be achieved. The present invention, therefore, is directed to a method of imaging for prostate cancer in a patient. The method of imaging includes contacting an androgen receptor with the radiolabeled non-steroidal compound under conditions effective to bind the radiolabeled non-steroidal compound to the androgen receptor, and detecting the presence of any radiolabeled non-steroidal compound bound to the androgen receptor. Thus, an image of the prostate tumor cells with the radiolabeled compound bound to the tumor cells is obtained.

The compounds herein may be made up in any suitable form appropriate for the desired use; e.g., oral, parenteral (for example, subcutaneously, intravenously, intramuscularly, intraperitoneally, by intranasal instillation, or by application to mucous membranes, such as that of the nose, throat, and bronchial tubes, or by instillation into hollow organ walls or newly vascularized blood vessels) or topical administration. Suitable dosage forms for oral use include tablets, dispersible powders, granules, capsules, suspensions, syrups, and elixirs. The compounds may be administered alone or with suitable pharmaceutical diluents or carriers. Inert diluents and carriers for tablets include, for example, calcium carbonate, sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art.

It will be appreciated that the actual preferred amount of the compound to be administered according to the present invention will vary according to the particular compound, the particular composition formulated, and the mode of administration. Many factors that may modify the action of the inhibitor can be taken into account by those skilled in the art; e.g., body weight, diet, time of administration, route of administration, rate of excretion, condition of the subject, drug combinations, and reaction sensitivities and severities. Administration can be carried out continuously or periodically within the maximum tolerated dose. Optimal administration rates for a given set of conditions can be ascertained by those skilled in the art using conventional dosage administration tests.

Because the radiolabeled non-steroidal compounds of the present invention bind to the AR and prostate cancer cells contain significantly higher levels of AR than surrounding non-cancerous cells, it is possible to obtain an image of prostate cancer cells to which the radiolabeled non-steroidal compounds have bound. Detection of the radiolabeled non-steroidal compounds which have bound to the AR is performed using, for example, single-photon emission computed tomography, positron emission tomography, or other equivalent detection systems to obtain an image of the prostate cancer. The detection occurs through the measurement of radioactive emissions by the compounds of the present invention.

Another aspect of the present invention relates to methods of producing the radiolabeled non-steroidal compounds of the present invention. The acylanilides of the invention may be manufactured by any chemical process known to be suitable for the manufacture of chemically-analogous compounds. Examples of suitable chemical processes for manufacturing acylanilides are shown in U.S. Pat. No. 4,636,505 to Tucker, which is hereby incorporated by reference.

To synthesize the radiohalogenated AR ligands, a variety of precursors can be used which have the formula shown below:

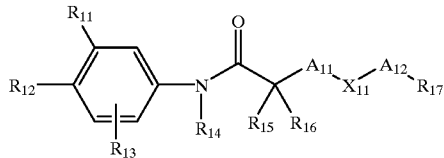

wherein $R_{11}$, $R_{12}$ and $R_{13}$, are the same or different, and each is a hydrogen, a halogen, a nitro, a cyano, a carbamoyl, a perfluoroalkyl, a haloalkylamido, an isothiocyanate, an azide, a diazocarbonyl, a substituted oxirane, a β-chloroethylamine, a diazonium salt, a triazene group, a tertiary alklyl group, an oxy group, an alkoxy group, a stannoalkyl group, a stannoaryl group, an unsubstituted or substituted boronic acid, an alkyl silane group, a pentaflourosilicate group, an alkylgermano group, a halomercury group, a trifluoroacetylthallate group, a thallium difluoride group, or other defined substituents;

$R_{14}$ is a hydrogen, an alkyl, or is joined to $R_{15}$;

$R_{15}$ is a hydrogen, a hydroxy, an alkyl, a haloalkyl, an alkoxy, an acyloxy, an amino, an alkylamino, a thiol, a thioalkyl, a halogen, or is joined to $R_{14}$ or $X_{11}$;

$R_{16}$ is a hydrogen, an alkyl, a halogen, or a haloalkyl;

$A_{11}$ and $A_{12}$ are the same or different, and each is a direct link or alkylene;

$X_{11}$ is a halogen, an oxygen, a sulfur, a sulphinyl, a sulfonyl, an amino, or an alkylimino, an alkylene, or is joined to $R_{15}$ directly, through an oxirane ring, through an $SO_2$ group, or through an $SO$ group;

$R_{17}$ is an aryl ring, substituted at different positions with a hydrogen, a halogen, a diazonium salt, a triazene group, a tertiary alkyl amino group, a nitro group, an oxy or an alkoxy group, an amino or an alkylamino group, a stannoalkyl group (Sn—Alk$_3$), a stannoaryl group (Sn—Ar$_3$), an unsubstituted or a substituted boronic acid, an alkyl silane group (—SiR$_3$), a pentafluorosilicate (—SiF$_5$) group, an alkylgermano group (—GeAlk$_2$), a halomercury group (—HgHal), a trifluoroacetyl thallate group, or a thallium difluoride group.

The precursors are reacted with suitable compounds under conditions effective to produce the radiolabeled non-steroidal compounds of the present invention. Generally, such suitable compounds contain a radioactive component (e.g., $^{3}H$, $^{18}F$, $^{125}I$, $^{123}I$, or other radiohalogens), which may be bound to the precursor in the step immediately preceding formation of the compounds of the present invention, and may include radioactive halide salts, hydrohalide acids, or elemental halides containing any isotope suitable for imaging.

For example, the precursors used for radiohalogenation can be precursors for aromatic nucleophilic substitution (i.e., aryl diazonium salts, aryl triazenes, tertiary aromatic alkyl amines, nitroaryl precursors, aryl halides); precursors for aromatic electrophilic substitution (i.e., aryl stannanes Ar—SnR$_3$, aryl boranes Ar—BR$_2$, aryl silanes (Ar—SiR$_3$), organopetnafluorosilicates (Ar—SiF$_5$K$_2$), aryl germanes Ar—GeR$_2$, aryl mercuriates Ar—HgCl, aryl thallates Ar—Tl(OCOCF$_3$)$_2$, Ar—H (direct halogenation ortho- or para- to NH$_2$, or OH)); precursors for aliphatic nucleophilic substitution (i.e., triflates, mesylates and tosylates, trifluoroacetates, epoxides, cyclic sulfates, alcohols, alkyl halides); or precursors for aliphatic electrophilic substitution (i.e., Alk-BMe$_3$).

Examples of preferred reactions are as follows:

Aryl Diazonium Salts in Preparation of Aromatic Radiohalogenated AR Ligands

As shown in the scheme below, aromatic diazonium salts are useful precursors for radiohalogenation (Knoechel et al., "Development of a Non-Carrier Method For 18f-Labeling," *J. Labeled Comp. Radiopharm.*, 38:325–36 (1996); Muller et al., "Synthesis of [18F]NNC," *Appl. Radiat. Isot.*, 46:323–28 (1995)). This so-called Sandmeyer reaction requires use of copper salts as a catalyst. The use of diazonium salts is described in Berridge et al., "Aromatic Fluorination With N.C.A. 18F-Fluoride: A Comparative Study," *J. Labeled Compd. Radiopharm.*, 22:687–94 (1985).

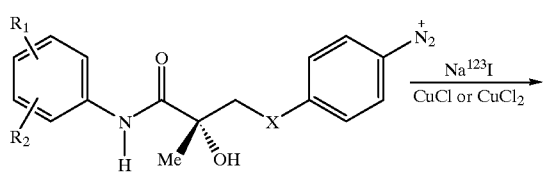

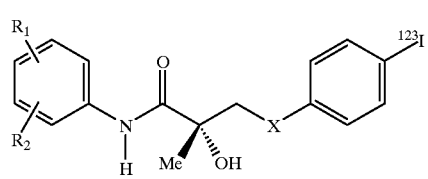

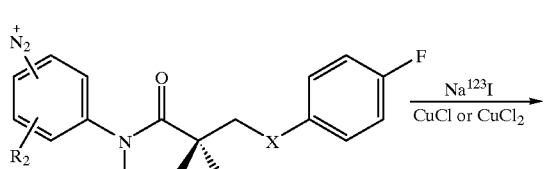

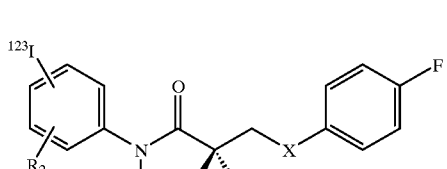

According to Ng et al., "Aromatic Fluorinations Suitable For Fluorine-18 Labeling of Estrogens," *J. Org. Chem.,* 46:2520–28 (1981), decomposition of tetraphenylborate diazonium salts gives fluorinated product. This reaction can be used for radiofluorination as illustrated below, where HF is a radiolabeled acid.

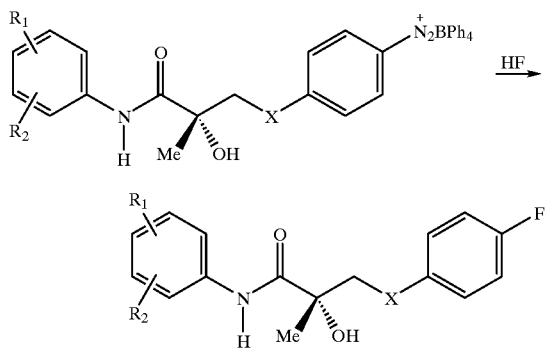

Aryl Triazenes in Preparation of Aromatic Radiohalogenated AR Ligands

The scheme below shows the preparation of $[^{125}I]$- and $[^{123}I]$-radioiodinated or $[^{18}F]$-radiofluorinated compounds. In this scheme, acid-catalyzed nucleophilic substitution of triazene leads to the final radioiodinated ligands. This procedure is described in Counsell (Van Dort et al., "Radioiodinated P-Iodoclonidine: A High-Affinity Probe For The Alpha 2-Adrenergic Receptor," *J. Med. Chem.,* 30:1241–44 (1987)).

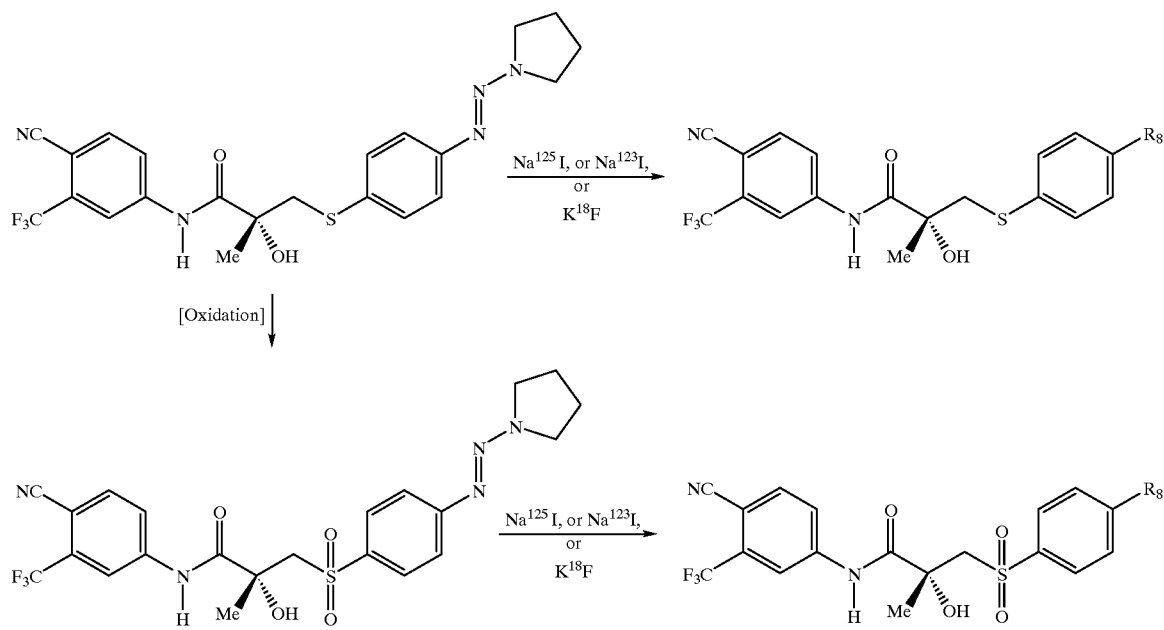

where $R_8$ is a phenyl substituent as set forth above, preferably a radiohalide.

Piperidiene triazenes also can be used for radiohalogenation. Unfortunately, described yield of radiofluorination was very low (<4%) in the case of the reaction in DMSO at 180° C. in the course of preparation of the analog of MPTP (Berridge et al., "Design and Synthesis of 18F-Labeled Neurotoxic Analogs of MPTP," *J. Med. Chem.*, 36:1284–90 (1993)) and in model reactions (Berridge et al., "Aromatic Fluorination with n.c.a. 18F-fluoride: A Comparative Study," *J. Labeled Campd. Radiopharm.*, 22:687–94 (1985); Kilboum et al., "Carrier-added and No-carrier-added Syntheses of [18F]spiroperidol and [18F]haloperidol," *Int. J. Appl. Radiat. Isot.*, 35:591–98 (1984)). Moderate yields (0–43%) of fluorinated products have been obtained by decomposition of piperidino triazenes in HF (Ng et al., "Aromatic Fluorinations Suitable for Fluorine-18 Labeling of Estrogens," *J. Org. Chem.*, 46:2520–28 (1981)). The use of triazene derivatives for [$^{18}$F]radiofluorination, [$^{78}$Br, $^{77}$Br]radiobromination, and [$^{125}$I]radioiodination is described in U.S. Pat. No. 4,431,627 to Eckelman et al. Fluorination using triazene as a precursor is described in Tewson et al., "Preparation of Fluorine-18 Aryl Fluorides: Piperidyl Triazenes as a Source of Diazonium Salts," *J. Chem. Soc., Chem. Commun.*, 1149–50 (1979) and Berridge et al., "Aromatic Fluorination with n.c.a. 18F-fluoride: A Comparative Study," *J. Labeled Campd. Radiopharm.*, 22:687–94 (1985).

Tertiary Aromatic Alkyl Amines in Preparation of Aromatic Radiohalogenated AR Ligands Aromatic tertiary alkyl amines can be displaced with halogen. This method was used in the preparation of radiofluorinated GABA$_A$-gated chlorine ion exchange blocker (DMSO, 135° C., Kryptofix, NA$^{125}$I,) (Snyder et al., "Synthesis of Carbon-11, Fluorine-18, and Iodine-125-," *J. Med. Chem.*, 38:2663–71 (1995)), and can be used for radiofluorination of AR ligands according to the scheme below.

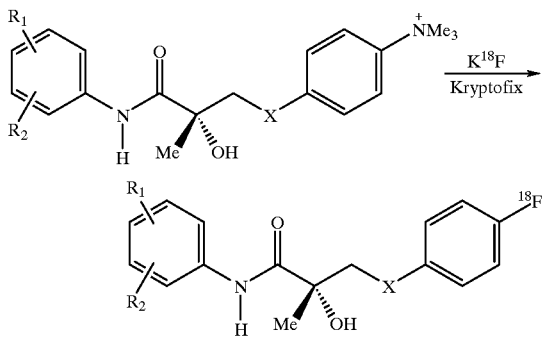

Nitroaryl Precursors Ar-NO$_2$ in Preparation of Aromatic Radiohalogenated AR Ligands Aromatic nitro compounds are used for substitution for fluorine. This method was described in Kilbourn et al., "Fluorine-18 Labeling of Proteins," *J. Nucl Med.*, 28:462–70 (1987); Hwang et al., "A New Procedure for Labeling Alkylbenzenes with [18F]fluoride," *Int. J. Rad. Appl. Instrum.[A],* 42:1043–47 (1991). Yields from good (53–85%) to poor (2–9%) have been obtained with use of Bu$_4$NH$^{18}$F (TBA.$^{18}$F) as a carrier of fluorine-18 (Kilbourn et al., "Carrier-added and No-carrier-added Syntheses of [18F]spiroperidol and [18F]haloperidol," *Int. J. Appl. Radiat. Isot.*, 35:591–98 (1984)). Nucleophilic displacement of aromatic nitro group has been widely studied in Attina et al., "Labeled Aryl Fluorides from the Nucleophilic Displacement of Activated Nitro Group by 18F-F-," *J. Label. Comp. Radiopharm.* 20:501–14 (1983). For radiofluorination, the scheme below is appropriate.

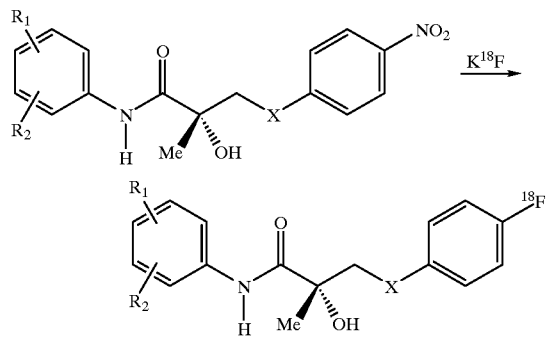

Aryl Halides in Preparation of Aromatic Radiohalogenated AR Ligands

Halogen Exchange Reactions

Aromatic halogens can be exchanged with the same but radioactive halogen atom (homoexchange), or another radioactive halogen (heteroexchange) atom at elevated temperatures.

The exchange of iodine atom on $^{125}$I has been described for 3,5-diiodothirosine in an aqueous solution at 99° C. in Breslav et al., In *American Peptide Symposium*, 14th; Columbus, Ohio, (1995), and in the presence of ammonia sulphate (NH)$_4$SO$_4$ and Na$^{125}$I at 145° C. (Snyder et al., "Synthesis of Carbon-11, Fluorine-18, and Iodine-125," *J. Med. Chem.*, 38:2663–71 (1995)). For radiohalogenation, the scheme below is appropriate.

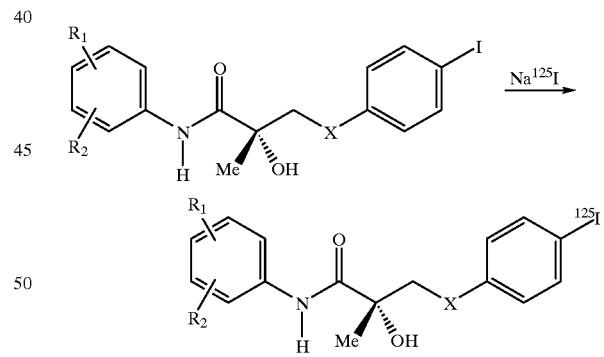

Exchange of iodine in preparation of radioiodinated lipids is described in Meyer et al., "Potential Tumor or Organ-Imaging Agents. Radioiodinated Phospholipid Ethers," *J. Med. Chem.*, 32:2142–7 (1989); Counsell et al., "Tumor Visualization with a Radioiodinated Phospholipid Ether," *J. Nucl. Med.* 31:332–36 (1990); Seevers et al., "Potential Tumor," *J. Med. Chem.*, 25:1500–03 (1982). The same reaction is described in DeGalan et al., "Iodine-125 Cholesteryl Iopanoate for Measuring Extent of Artherosclerosis in Rabbits," *J. Nucl. Med.*, 29:503–8 (1988); Counsell et al., "Lipoprotein Incorporation Enhances Radioiodinated Cholesteryl Ester Uptake into Steroid Hormone-Secreting Tissues," *J. Nucl. Med.*, 30:1088–94 (1989); Plotzke et al., "Selective Localization of Radioiodinated Alkylphosphocholine Derivatives in Tumors," *Int. J. Rad. Appl. Instrum.* [B], 19:765–73 (1992).

The exchange of an iodine atom for $^{18}F$ has been described in Berridge et al., "Aromatic Fluorination with n.c.a. 18F-fluoride: A Comparative Study," *J. Labeled Compd. Radiopharm.*, 22:687–94 (1985). The scheme below is appropriate for radiofluorination.

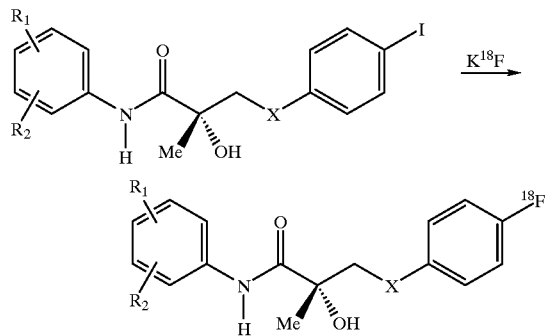

A single-step procedure for bromine-iodine exchange has been proposed in Ceuster et al., "New Single-Step Radioiodination," *J. Org. Chem.*, 60:8324–26 (1995). A similar approach can lead to radioiodinated AR ligands of the present invention, as shown below.

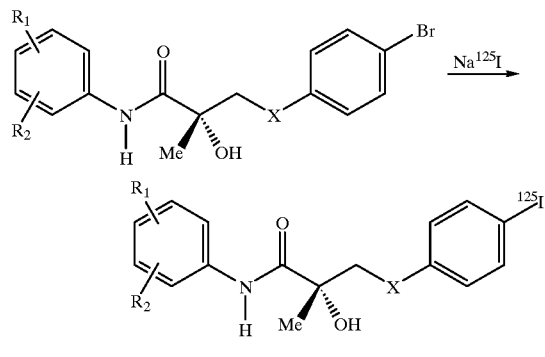

The exchange of aromatic bromide for $^{18}F$ has been described in Berridge et al., "Aromatic Fluorination with n.c.a. 18F-fluoride: A Comparative Study," *J. Labeled Compd. Radiopharm.*, 22:687–94 (1985). The scheme below is appropriate for radiofluorination.

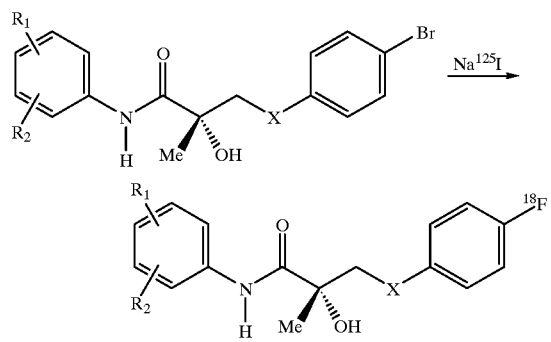

A chlorine-fluorine exchange as described in Kilbourn et al., "Carrier-added and No-carrier-added Syntheses of [18F] spiroperidol and [18F]haloperidol," *Int. J. Appl. Radiat. Isot.*, 35:591–98 (1984) as shown below may be used for radiofluorination.

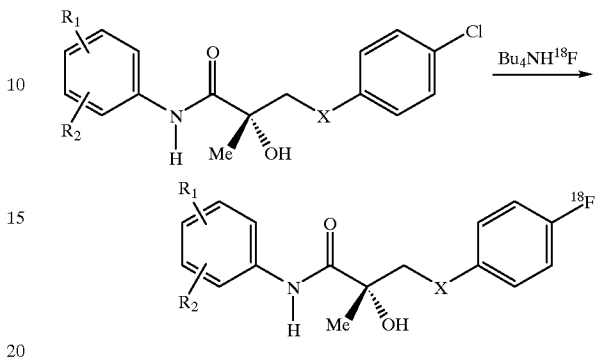

Fluorine-fluorine exchange as described by Kilbourn et al., "Carrier-added and No-carrier-added Syntheses of [18F] spiroperidol and [18F]haloperidol," *Int. J. Appl. Radiat. Isot.*, 35:591–98 (1984) as shown below may be used to prepare radiofluorinated product. This reaction was also described in Attina et al., "Labeled Aryl Fluorides from the Nucleophilic Displacement of Activated Nitro Group by 18F-F-," *J. Label. Comp. Radiopharm.*, 20:501–14 (1983).

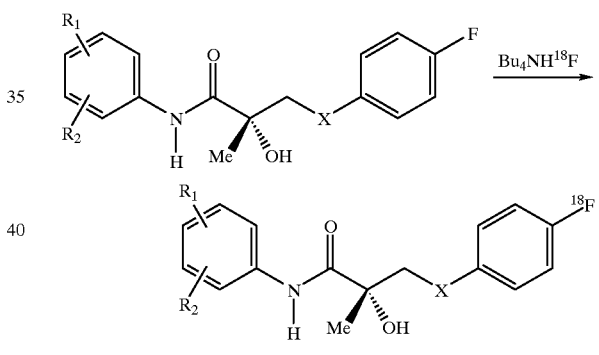

Aryl Stannanes in Preparation of Aromatic Radiohalogenated AR Ligands

The scheme below shows the use of tributyltin precursor for the synthesis of radioiodinated AR ligands. (John et al., "Synthesis and Pharmacological," *Cancer Res.*, 55:3022–27 (1995); ((Mais et al., "Novel Synthesis and Biochemical Properties," *J. Med. Chem.*, 34:1511–14 (1991)) Gallant et al., In *ACS Meeting*. 209th; ACS: Anaheim, Calif. Apr. 2–6, 1995 pp. MEDI-171 (1995)); Hodson et al., "Regiospecific Synthesis," *Perkin Trans.* 1, 2965–68 (1995); Wardell et al., "Reactions of Aromatic Sulfenyl Compounds with Organotin Compounds," *J. Organomet. Chem.*, 78:395–404 (1974)).

The advantages of these precursors in the incorporation of radiohalogens are their easy preparation and chemical stability. However, they are highly toxic (Kabalka, "The Synthesis of Radiolabeled Compounds Via Organometallic Intermediates," *Tetrahedron*, 45:6601–21 (1989)).

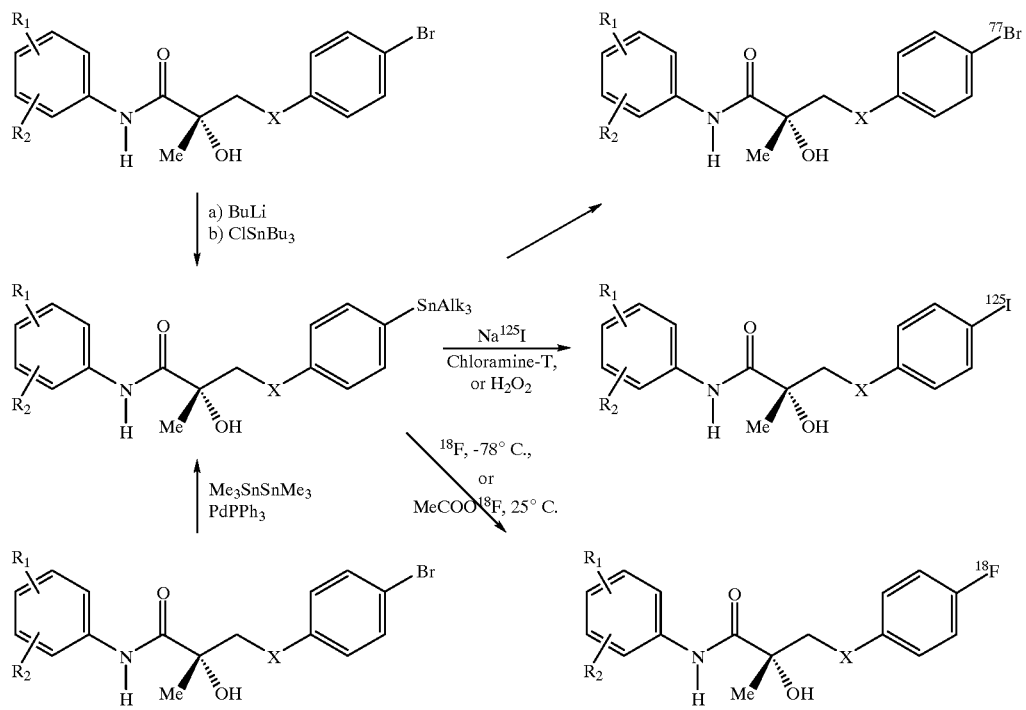

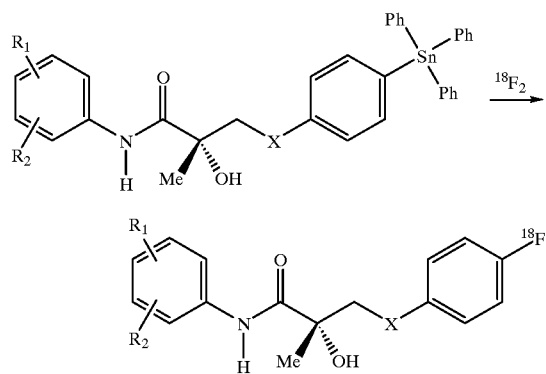

As shown below, triphenyltin derivatives can be reacted with elemental fluorine for radiofluorination according to a procedure described in Berridge "Chemistry of Fluorine-18 Radiopharmaceuticals," *Appl. Radiat. Isot.*, 37:685–93 (1986).

Aryl Boranes in Preparation of Aromatic Radiohalogenated AR Ligands

The iodination of an aromatic ring can be achieved via the direct reaction of arylboronic acid with radiolabeled sodium iodide in the presence of an oxidizing agent (Kabalka, "The Synthesis of Radiolabeled Compounds Via Organometallic Intermediates," *Tetrahedron*, 45:6601–21 (1989). Similar precursors can be used for [$^{18}$F]-radiobromination, [$^{77}$Br]-radiochlorination, and [$^{34m}$Cl]-radiochlorination.

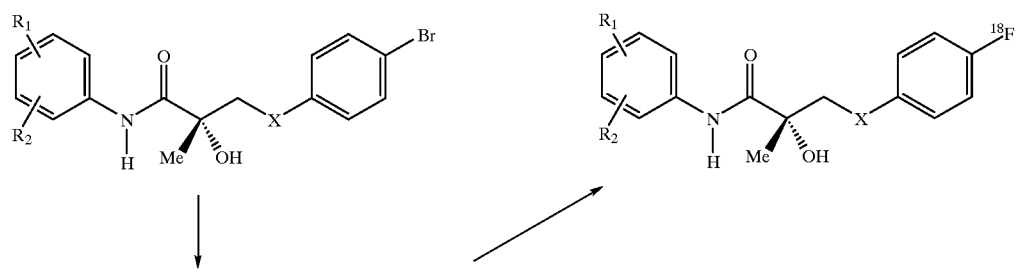

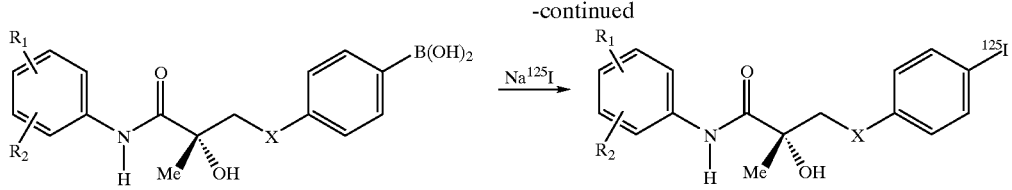

Aryl Silanes (Ar—SiR₃), and Organopentafluorosilicates (Ar—SiF₅K₂) in Preparation of Aromatic Radiohalogenated AR Ligands Arylsilanes shown below are valuable precursors for radiohalogenation under a variety of conditions and forms of halogen used (Kabalka, "The Synthesis of Radiolabeled Compounds Via Organometallic Intermediates," *Tetrahedron*, 45:6601–21 (1989)).

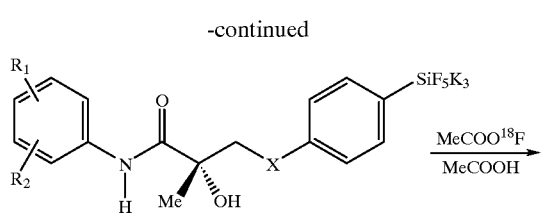

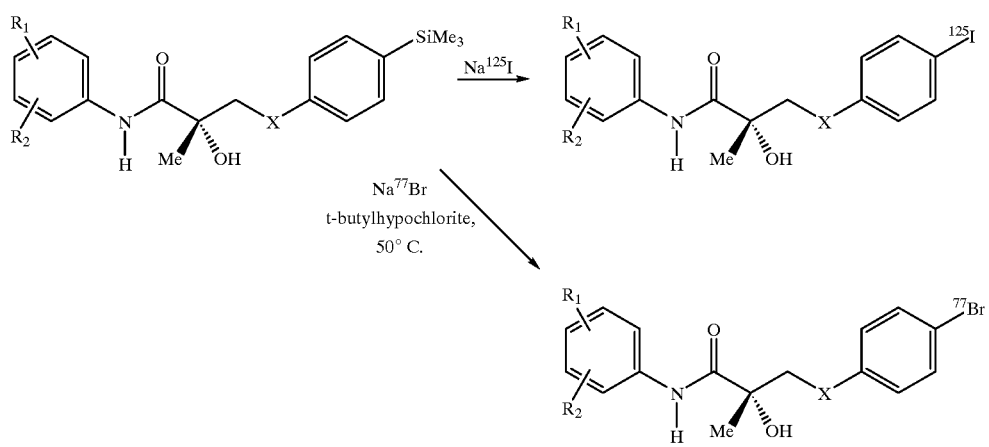

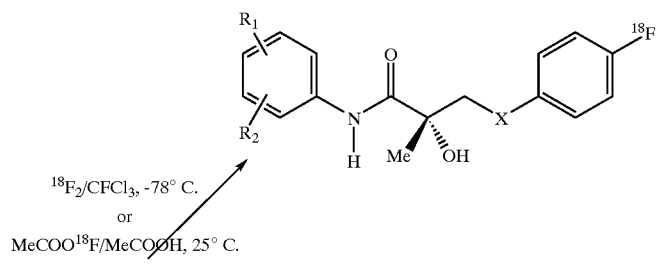

Organopentafluorosilicates are air and moisture stable precursors of radiohalogenated compounds (Kabalka, "The Synthesis of Radiolabeled Compounds Via Organometallic Intermediates," *Tetrahedron*, 45:6601–21 (1989)). They can be used for preparation of the AR radioligands, according to the scheme below.

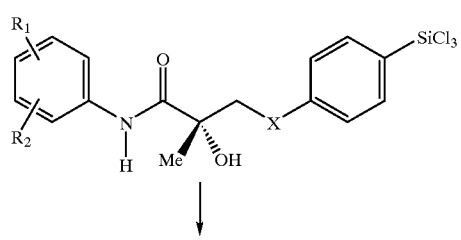

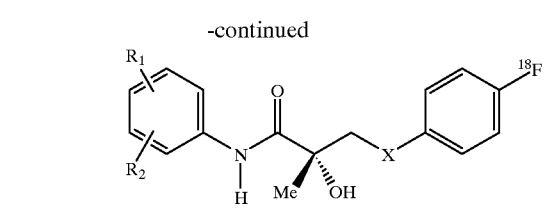

Aryl Germanes (Ar—GeR₂) in Preparation of Aromatic Radiohalogenated AR Ligands Aryl germanes are chemically stable and low-toxic intermediates of aromatic radioiodination and radiobromination (Kabalka, "The Synthesis of Radiolabeled Compounds Via Organometallic Intermediates," *Tetrahedron*, 45:6601–21 (1989)). Their use for synthesis of radiohalogenated AR ligands is shown below.

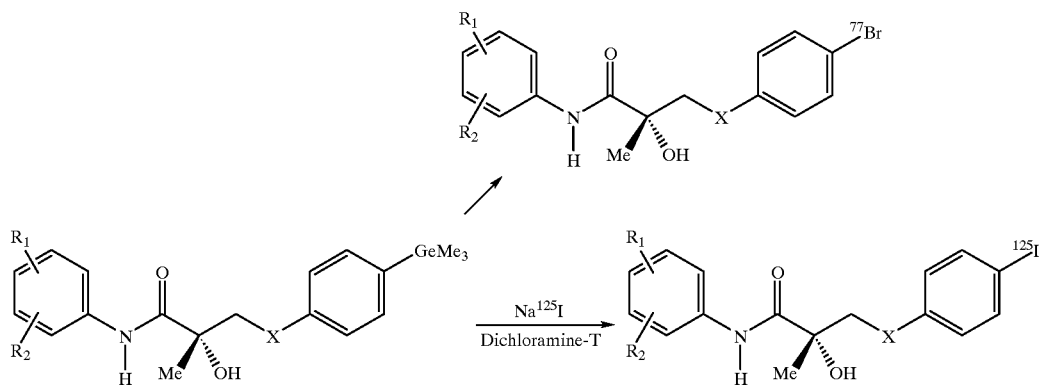

Aryl Mercuriates in Preparation of Aromatic Radiohalogenated AR Ligands

A tributyltin precursor is used as shown below for the synthesis of radioiodinated AR ligands. The advantage of these precursors in the incorporation of radiohalogens are their easy preparation and chemical stability. However, they are highly toxic (Kabalka, "The Synthesis of Radiolabeled Compounds Via Organometallic Intermediates," *Tetrahedron*, 45:6601–21 (1989)).

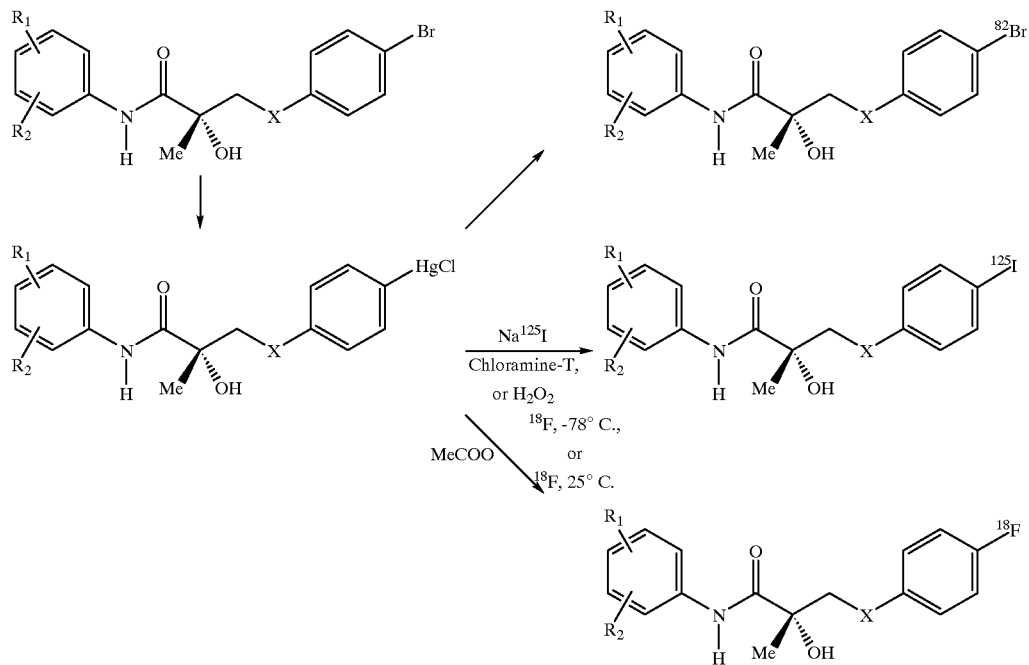

Aryl Thallates Ar—Tl(OCOCF$_3$)$_2$ in Preparation of Aromatic Radiohalogenated AR Ligands Aryl thallates can be prepared by predominantly para-substitution in an aromatic ring (Kabalka, "The Synthesis of Radiolabeled Compounds Via Organometallic Intermediates," *Tetrahedron*, 45:6601–21 (1989)). In the case of an aromatic ring containing strong electron withdrawing substituents, thallation can be achieved in the meta-position. As shown below, the aryl thallates may be used to produce radiolabeled AR ligands.

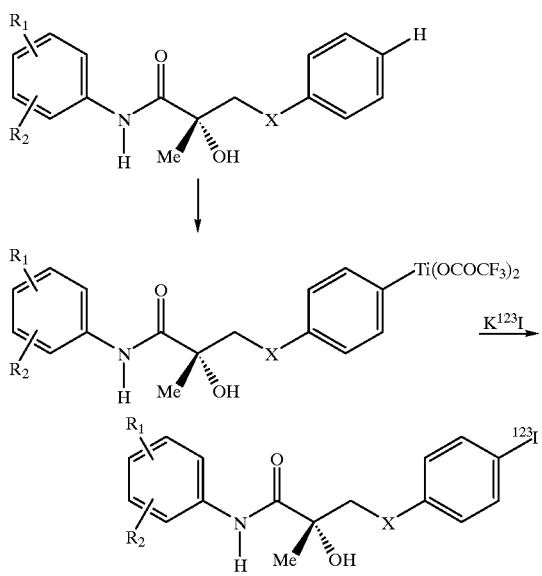

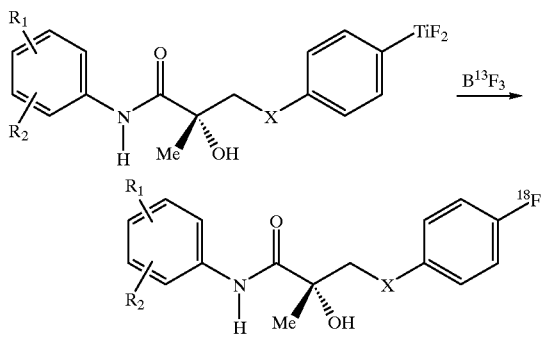

Arylthallium difluorides, shown below in the presence of boron trifluorides, can be decomposed to radiofluorides according to Taylor et al., *J. Org. Chem.*, 42:362 (1977).

Direct Halogenation

Direct fluorination has been done in the case of 4-borono-phenylalanine with $^{18}F_2$, or $MeCOO^{18}F$ as a source of fluorine (Ishiwata et al., "Synthesis and Radiation Dosimetry of 4-Borono-2-[18]fluoro-D,L-phenylalanine: A Target Compound for PET and Boron Neutron Capture Therapy," *Int. J. Rad. Appl. Instrum.* [A], 42:325–28 (1991); Reddy et al., "4-Borono-2-," *J. Labeled Comp. Radiopharm.*, 37:599 (1995)). Similarly, fluorination of an amino precursor can be carried out.

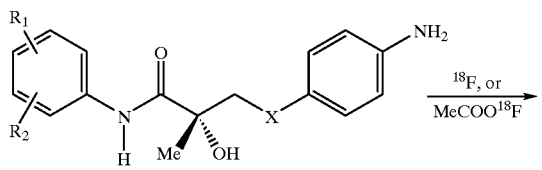

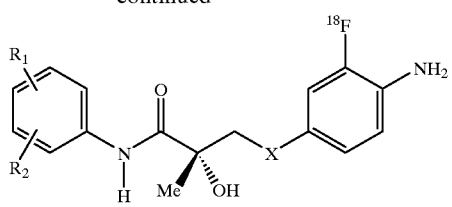

Direct iodination with $TlCl_3$ is described in Resek, "Photo-affinity Labeling," *J. Biol. Chem.*, 263:14410–16 (1988).

Triflates, Mesylates and Tosylates

Triflates and tosylates are used for nucleophilic displacement leading to a radiohalogenated product. Katzenellenbogen used triflates as precursors for [$^{18}F$]-fluorinated steroidal androgen receptor ligands in the synthesis of steroidal AR ligands (Liu et al., "Synthesis of High-Affinity Fluorine-Substituted Ligands for the Androgen Receptor: Potential Agents for Imaging Prostatic Cancer by Positron Emission Tomography," *J. Med. Chem.*, 35:2113–29 (1992); Liu et al., "Fluorine-18-labeled Androgens: Radiochemical Synthesis and Tissue Distribution Studies on Six Fluorine-Substituted Androgens, Potential Imaging Agents for Prostatic Cancer," *J. Nucl. Med.*, 33:724–34 (1992); Pomper et al., "11.beta.-Methoxy-, 11.beta.-Ethyl, and 17.alpha.-Ethynyl-substituted 16.alpha.-Fluoroestradiols: Receptor-Based Imaging Agents with Enhanced Uptake Efficiency and Selectivity," *J. Med. Chem.*, 33:3145–55 (1990)). Tetrabutylammonium [$^{18}F$] fluoride was the carrier for the radiohalogen. Thus, displacement of triflates with $K^{18}F$ described in Zhang et al., "Synthesis and Evaluation of Two," *J. Med. Chem.*, 39:5110–18 (1996) was performed according to [Kiesewetter, 1989 #4735]. Similarly, a precursor can also be easily prepared from iodide using commercially available silver triflate (e.g., silver trifluoromethanesulfonate, Aldrich Chemical Co., Milwaukee, Wis.). (See, also the procedure for mild etherification of alcohols with primary alkyl halides (*Tetrahedr. Lett.*, 35:8111 (1994); *Tetrahedr. Lett.*, 36:719 (1995)).

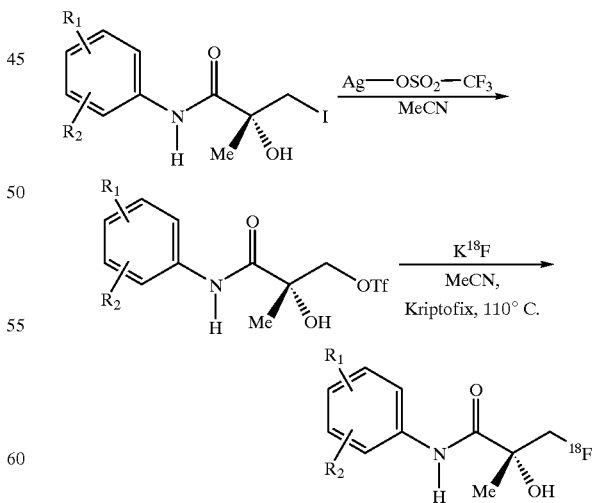

The use of mesylates as a precursor for fluorination is described in Kiesewetter et al., "Synthesis and Biological Properties of," *J. Med. Chem.*, 38:1711–19 (1995). The authors used $Me_4NHF_2$ as a source of [$^{19}F$]-fluorine. Methylates can be easily prepared from iodide (shown below) using commercially available silver mesylate (e g., methanesulfonic acid silver salt, Acros, Coral Gables, Fla.).

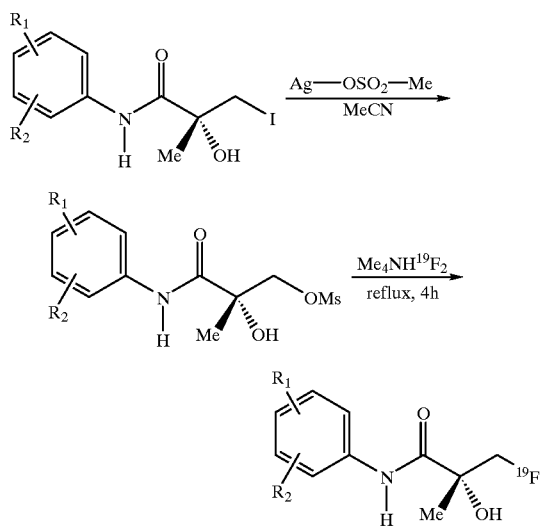

Trifluoroacetates

Aliphatic trifluoroacetates are used for fluorination of estradiols with $Bu_4NF$ as a source of fluorine (Pomper et al., "11.beta.-Methoxy-, 11.beta.-Ethyl, and 17.alpha.-Ethynyl-substituted 16.alpha-Fluoroestradiols: Receptor-Based Imaging Agents with Enhanced Uptake Efficiency and Selectivity," *J. Med. Chem.*, 33:3145–55 (1990)). As similar method can be applied to AR ligands.

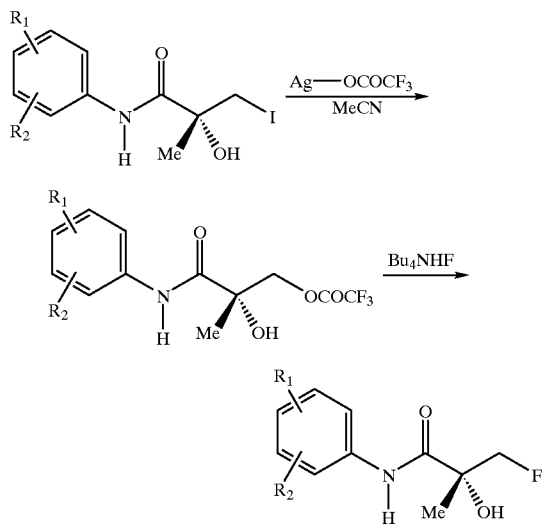

Epoxides

Opening of epoxides can be used for radiohalogenation as shown below.

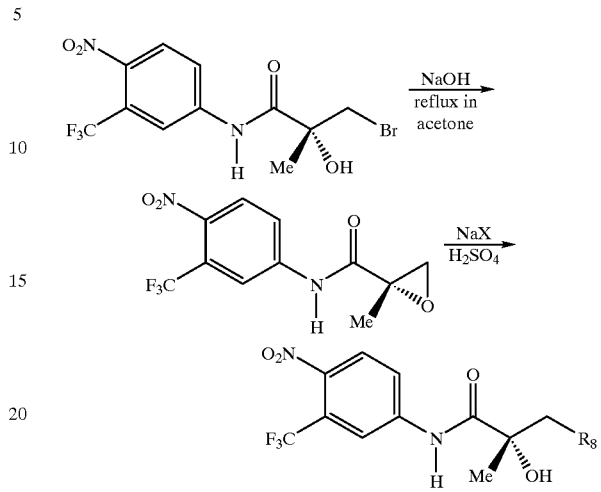

where $R_8$ is a phenyl substituent as set forth above, preferably a radiohalide.

Cyclic Sulfates

Katzenellenbogen used cyclic sulfates as precursors for radiofluorination of steroidal androgen receptor ligands metribolone (R1881) (Liu et al., "Fluorine-18-Labeled Androgens: Radiochemical Synthesis and Tissue Distribution Studies on Six Fluorine-Substituted Androgens, Potential Imaging Agents for Prostatic Cancer," *J. Nucl. Med.*, 33:724–34 (1992)), in the synthesis of steroidal AR ligands (Liu et al., "Synthesis of High-Affinity Fluorine-Substituted Ligands for the Androgen Receptor. Potential Agents for Imaging Prostatic Cancer by Positron Emission Tomography," *J. Med. Chem.*, 35:2113–29 (1992)). Tetrabutylammonium [$^{18}$F]fluroide was the carrier for the radiohalogen. Synthesis of cyclic sulfates is described in Liu et al., "Synthesis of High-Affinity Fluorine-Substituted Ligands for the Androgen Receptor. Potential Agents for Imaging Prostatic Cancer by Positron Emission Tomography," *J. Med. Chem.*, 35:2113–29 (1992). Cyclic sulfates are useful precursors for radiohalogenation to AR ligands.

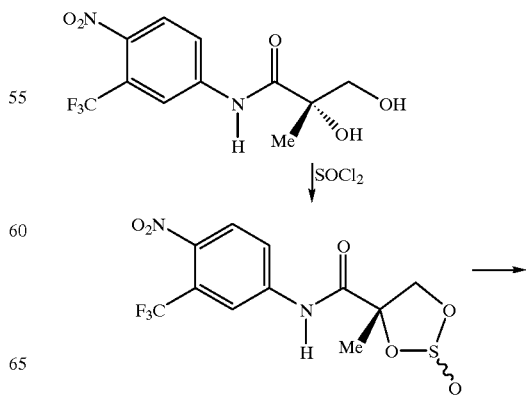

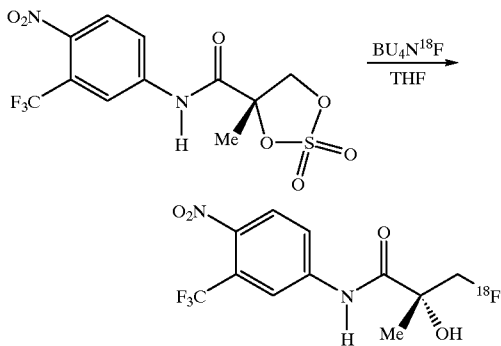

Exchange of Alcohols for Halogens

An iodinated compound can be prepared following the procedure of Hoyte et al., ("Synthesis and Evaluation of 7 alpha-iodo-5 alpha-dihydrotestosterone as a Potential Radioligand for Androgen Receptor," *J. Med. Chem.*, 37(8):1224–30 (1994) as shown below:

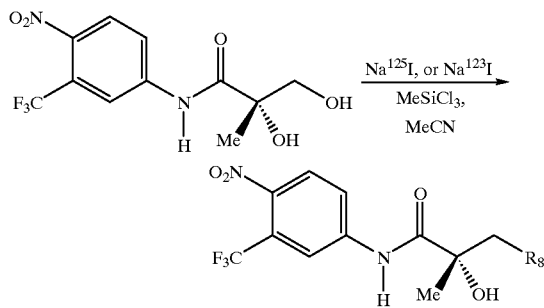

where $R_8$ is a phenyl substituent as set forth above, preferably a radiohalide.

Radiolabeled compounds can be prepared using the scheme shown below and described in Berridge et al., "Design and Synthesis of 18F-labeled Neurotoxic Analogs of MPTP," *J. Med. Chem.*, 36:1284–90 (1993); Berridge, "Chemistry of Fluorine-18 Radiopharmaceuticals," *Appl. Radiat. Isot.*, 37:685–93 (1986)); Liu et al., "Synthesis of High-Affinity Fluorine-Substituted Ligands for the Androgen Receptor. Potential Agents for Imaging Prostatic Cancer by positron emission tomography," *J. Med. Chem.*, 35:2113–29 (1992).

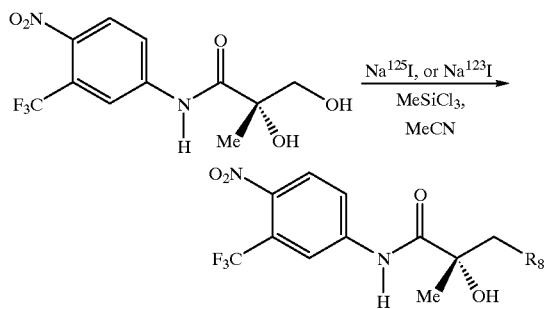

where $R_8$ is a phenyl substituent as set forth above, preferably a radiohalide.

Exchange of Halogens

The radiolabeled compounds of the present invention can be produced using the scheme shown below.

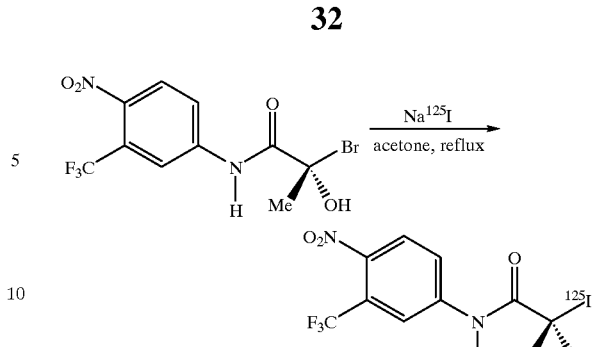

As shown below, the radiolabeled compound can be produced from alkyl bromides (Kiesewetter et al., "Synthesis and Biological Properties of," *J. Med. Chem.*, 38:1711–19 (1995); Berridge et al., "Design and Synthesis of 18F-Labeled Neurotoxic Analogs of MPTP," *J. Med. Chem.*, 36:1284–90 (1993). It is possible to displace aliphatic bromide for fluoride with potassium [$^{19}$F]fluoride and Kriptofix (Berridge, "Chemistry of Fluorine-18 Radiopharmaceuticals," *Appl. Radiat. Isot.*, 37:685–93 (1986); Goodman et al., "Synthesis of [18F]-N-3-Fluoropropyl-2-,", *J. Labeled Comp. Radiopharm.*, 35:432–434 (1994)).

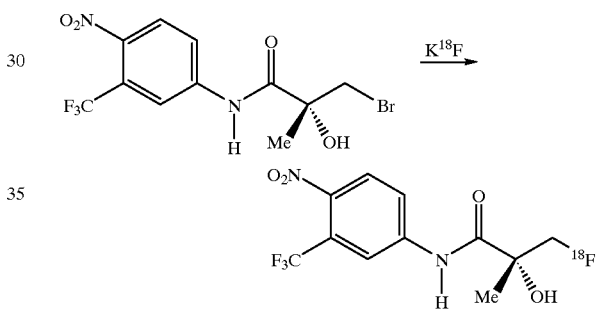

As shown below, radiolabeled compounds of the present invention can be obtained using the procedure described in Berridge et al., "Design and Synthesis of 18F-Labeled Neurotoxic Analogs of MPTP," *J. Med. Chem.*, 36:1284–90 (1993).

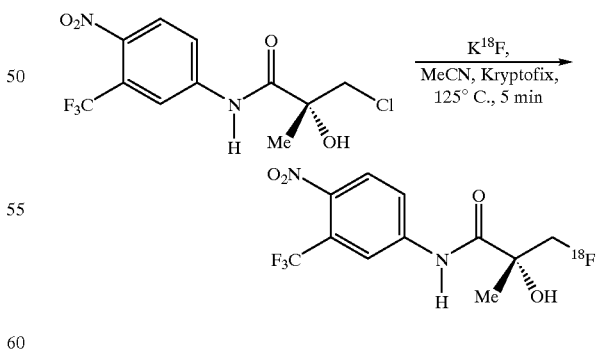

Aliphatic Organoboranes in Preparation of Radiohalogenated AR Ligands

As shown below, the radiolabeled compounds of the present invention can be obtained as described in Kabalka, "The Synthesis of Radiolabeled Compounds Via Organometallic Intermediates," *Tetrahedron*, 45:6601–21 (1989).

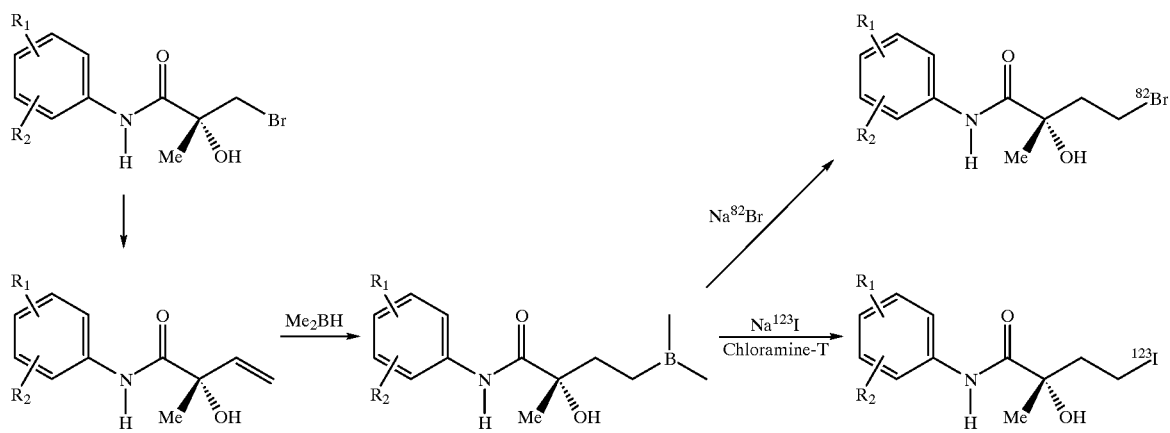

As shown in the schemes above, $R_6$ is a methyl group and $R_5$ is a hydroxy group. However, $R_5$ and $R_6$ may have any of the substituents as described above and the reaction schemes may be used to produce either the R or S isomers.

EXAMPLES

The following examples are provided to illustrate embodiments of the present invention, but are by no means intended to limit its scope.

Example 1

Synthesis of the R-Isomers of Iodinated Compounds

Iodinated compounds were synthesized as shown below, utilizing bromo acid as a key intermediate.

Aliphatic iodides and the aryl iodides were synthesized from this common intermediate. Since 4-iodothiophenol is not commercially available, it was synthesized by reduction of 4-iodobenzenesulfonyl chloride in a Sn/HCl system according to Backer et al., "Éthers Radiaires de l'Acide Tétrahioorthostannique II," *Rec. Trav. Chim.*, 53:1101–12 (1934). Oxidation of R-iodo-thio-Bicalutamide with m-choroperbenzoic acid gave the desired iodo analog.

Example 2

Synthesis of R-Isomers of Iodine Analogs of Hydroxyflutamide and Bicalutamide

Non-radioactive R-isomers were synthesized as described in the reaction scheme below.

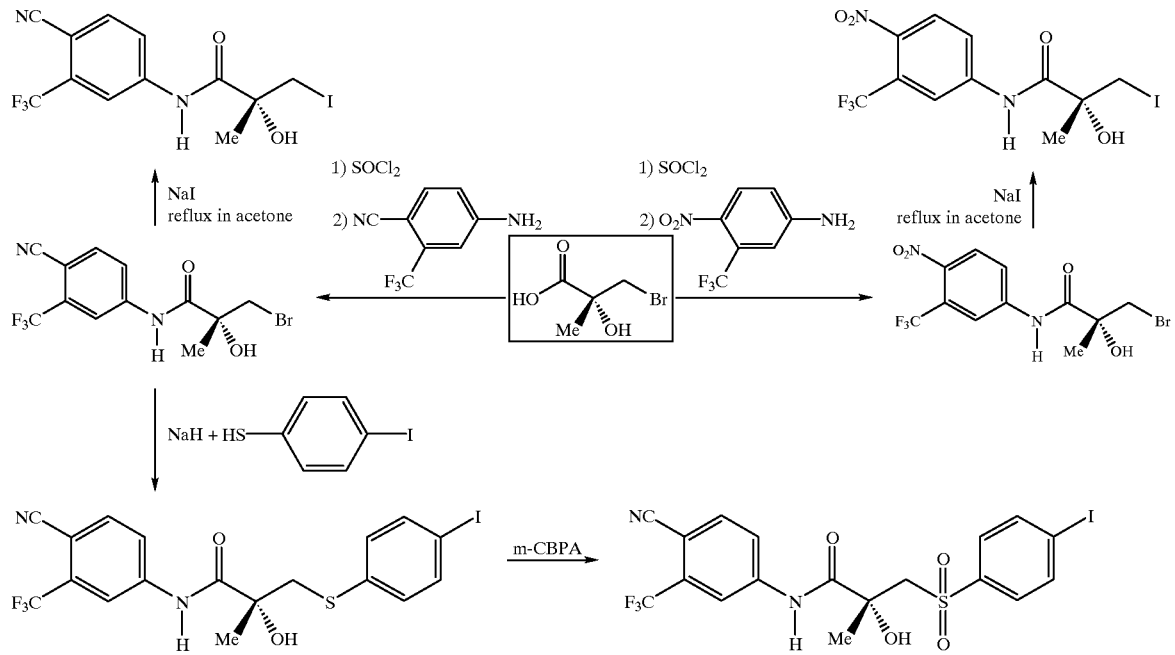

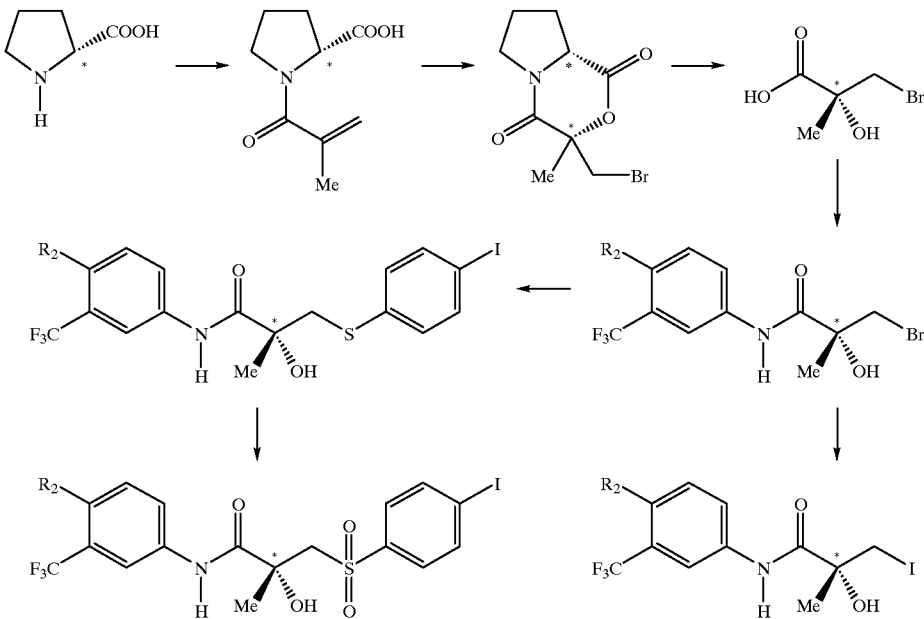

where $R_2$ is $NO_2$ or CN.

To synthesize "cold" (unlabeled) iodinated AR ligands, a reaction sequence applied for preparation of S-Bicalutamide (Tucker 1988a; Tucker 1988b) was modified by starting with R-proline as the chiral auxiliary. Thus, bromo-acid, a critical intermediate, was obtained as a pure enantiomer. R-proline was coupled with methacryloyl chloride under Schotten-Baumann conditions in aqueous acetone at 5–15° C. Terashima asymmetric bromolactonization (Jew et al., "Asymmetric Synthesis of Optically Active a,a-Substituted-a-Hydroxy Acid from a,b-Unsaturated Acids by the Novel Use of Halolactonization Reaction," *Tetrahedron* 35:2337–43 (1979); Nishihara et al., "Conformation of Methacryloyl-1-proline," *Bull. Chem. Soc. Japan*, 46:3894–5 (1973)) was used to prepare bromolactone with good yield by reaction of prolinamide with NBS in DMF at room temperature. Hydrolysis of bromolactone in 24% HBr under reflux for 1 hour gave rise a bromo-acid with high yield. Coupling of chloroanhydride of bromo acid, obtained in situ by reaction of bromo acid with thionyl chloride in DMA at approximately −10° C., with 4-nitro-3-trifluoromethylaniline or 4-cyano-3-trifluoromethylaniline gave rise to anilides, where $R_2$ is $NO_2$ or CN. Reaction of the former anilides with iodothiophenol, ionized by sodium hydride, was carried out in THF at room temperature. Since 4-iodothiophenol is not commercially available, it was prepared by reduction of 4-iodobenzenesulfonyl chloride by tin in HCl solution according to Backer et al., "Éthers Radiaires de l'Acide Tètrahioorthostannique II," *Rec. Trav. Chim.*, 53:1101–12 (1934). The product of the reaction, an iodinated AR ligand, was oxidized by peracetic acid in acetone or ethylacetate at room temperature to form another iodinated AR ligand with the substituent $R_2$ as described above. Aliphatic iodinated anilides were prepared using bromine/iodine exchange reaction by reflux of anilides in acetone with the presence of approximately a 20-fold excess of sodium iodide for 4 days.

Example 3

Binding Affinity of Lodinated & Fluorinated Compounds

AR binding affinities of the synthesized ligands were determined by competitive binding in the presence of the high affinity AR ligand, $^3$H-mibolerone ("$^3$H-MIB"). In preliminary experiments, the equilibrium dissociation constant (Kd) of MIB was determined at 4° C. for 18 hours by incubating increasing concentrations of $^3$H-MIB (0.01 to 10 nM) with cytosol. The minimum concentration of $^3$H-MIB to saturate AR sites in the cytosol preparation was 1 nM. AR binding studies for the ligands of interest were then performed under identical conditions by incubating increasing concentrations ($10^{-3}$ nM to 10,000 nM) of each ligand with cytosol and a saturating concentration of $^3$H-MIB (1 nM). The incubate also contained 1 μM triamcinolone to prevent interaction of $^3$H-MIB with glucocorticoid and progesterone receptors (Carlson and Katzenellenbogen, *J. Steroid Biochem.* 36:549–61 (1990)). For the determination of nonspecific binding, separate experiments were conducted by adding 1,000 nM MIB to the incubate. Unless otherwise indicated, all experiments were repeated three times or more. Separation of bound and free radioactivity at the end of incubation was achieved by the HAP method, as previously described (Mukherjee, et al., *Xenobiotica* 26:117–22 (1996)), and 0.8 mL of the ethanolic supernatant was added to 5 mL of scintillation cocktail. Radioactivity was counted in a liquid scintillation counter (Model LS6800, Beckman Instruments Inc., Palo Alto, Calif.).

To determine the Kd of MIB, data were analyzed using a modified form of the Scatchard equation:

$$B/F = -(B/Kd) + B_{max}/Kd \qquad \text{(Equation 1)}$$

where B was the concentration of specifically-bound $^3$H-MIB in the incubate, F was the concentration of free $^3$H-MIB in the incubate, and $B_{max}$ was the maximum concentration of $^3$H-MIB specifically bound to AR, which is also the concentration of available AR binding sites in the incubate. Experimental data were computer-fit to equations using fortran subroutines written for PCNONLIN (SCI Software, Lexington, Ky.).

For competition binding experiments, competitive displacement curves were constructed for each ligand with percent specific binding (specific binding of $^3$H-MIB at a particular ligand concentration expressed as a percentage of the specific binding of $^3$H-MIB in the absence of ligand) on the vertical axis and ligand concentration on the horizontal axis. The ligand concentration that reduced the percentage of specific binding by 50% (IC$_{50}$) was determined by computer-fitting the data for each ligand to the following equation:

$$B=B_0\{1-(C/IC_{50}+C)\} \quad \text{(Equation 2)}$$

where B$_0$ is the specific binding of $^3$H-MIB in the absence of ligand, and C is the ligand concentration. Binding affinities of the ligands were then compared using the equilibrium dissociation constant (Ki) of each ligand, as calculated using the equation below:

$$Ki=\{(IC_{50}*Kd)/(L+Kd)\} \quad \text{(Equation 3)}$$

where Kd was the equilibrium dissociation constant of $^3$H-MIB as determined in Equation 1, and L was the concentration of $^3$H-MIB in the incubate (i.e., 1 nM). Low Ki values are associated with agonist activity. The relative binding affinity ("RBA") of each compound was calculated according to the equation below:

$$RBA=\{(IC_{50} \text{ of } DHT)/(IC_{50} \text{ of a ligand})\}*100\% \quad \text{(Equation 4)}$$

The structures and AR binding affinities of these compounds are shown in FIG. 1 and Table 3 below. AR binding affinities for testosterone and R-bicalutamide are included for comparison. Ligands must demonstrate high selectivity and affinity for the AR in order to compete effectively for ARs in vivo (and thus be useful for imaging). In agreement with previous studies, significantly greater AR binding affinity was observed for the R-isomers than for their respective S-isomers. Each of the S-isomers tested showed poor AR binding affinity, with K$_i$ values greater than 100 nM. Also a higher degree of stereoselectivity was noted for the synthesized iodinated compounds, as compared to bicalutamide. The K$_i$ values for the R-isomers of iodinated compounds were two orders of magnitude lower than that of their respective S-isomers (Table 3).

TABLE 3

| Substituents | | | | |
|---|---|---|---|---|
| R$_8$ | X | Name | R-isomers Ki (nM) | S-isomers Ki (nM) |
| I | S | Compound 1 | 3.4 | 250 |
| I | SO$_2$ | Compound 2 | 3.1 | 3500 |
| F | S | Compound 3 | 1.8 | 70 |
| F | SO$_2$ | Compound 4 (Bicalutamide) | 11.0 | 365 |
| | | Testosterone | 1.1 | |

This high degree of stereoselectivity with the iodo-derivatives was unexpected, and reinforces the rationale for the use of iodinated compounds of the present invention. R-isomers of Compound 2 and its un-oxidized precursor, Compound 1, demonstrated high AR binding affinity. The K$_i$ value of the R-isomer for Compound 2 is 73% lower than that of R-Bicalutamide, and more importantly, comparable to that of the endogenous ligand testosterone. Thus, incorporation of iodine at the para-position not only allows for the introduction of alternative radionuclides for imaging, but also increases the AR binding affinity in this series of compounds. This is particularly noteworthy, in that it shows that Compounds 1 and 2 satisfy the primary requirement for in vivo AR-imaging (i.e., selective, high affinity AR binding).

A potential concern with these compounds may be their lower binding affinity as compared to testosterone (i.e., nanomolar concentrations of a radioligand might be unable to effectively compete with endogenous testosterone for AR binding sites in vivo). To that end, additional structural modifications were performed to obtain ligands with sub-nanomolar affinity for the AR. As shown in FIG. 1, incorporation of iodine and other halogens (e.g., fluorine, bromine) in other compounds of the present invention results in significantly higher AR binding affinity. Two of these compounds (K$_i$=0.82±0.13 and 1.6 nM[n=2], respectively) bind the AR with greater affinity than testosterone. Further, a brominated hydroxyflutamide derivative (R-bromo-hydroxyflutamide) was synthesized which has even greater AR binding affinity (K$_i$=0.30 nM, n=2). In addition, a fluorinated derivative of hydroxyflutamide can be an alternative ligand for in vivo AR imaging. It is hypothesized that the strong electron-withdrawing properties of fluorine will even further enhance the AR binding affinity and potential for in vivo imaging. In summary, there are several ligands with AR binding affinity similar to or greater than that of endogenous testosterone.

Carlson and Katzenellenbogen ("A Comparative Study of the Selectivity and Efficiency of Target Tissue Uptake of Five Tritium-labeled Androgens in the Rat," *J. Steroid Biochem.*, 36:549 (1990)) showed, however, that high affinity AR binding is not sufficient by itself to conclude that an agent may be useful for in vivo imaging. The rate of in vivo metabolism and clearance is also a critical factor determining tissue selectivity and distribution, in that agents which are more slowly metabolized are able to accumulate to a greater extent in target tissues (Carlson). Nothing is known about the in vivo metabolism and pharmacokinetics of compounds of the present invention. However, it is hypothesized that they are likely to undergo in vivo disposition like bicalutamide and flutamide. Previous studies with racemic $^{14}$C-labeled bicalutamide showed that the parent compound accounts for virtually all of the radioactivity in plasma (Cockshott et al., "The Pharmacokinetics of Casodex in Laboratory Animals," *Xenobiotica*, 21:1347–55 (1991)). Thus, circulating metabolites of the compounds of the present invention should contribute little to plasma and tissue concentrations during in vivo studies. In summary, the high AR binding affinity, the lack of significant binding affinity of non-steroidal ligands for other steroid receptors and SHBG, and proposed slow in vivo metabolism of these compounds make them ideal candidates for selective in vivo imaging of AR-positive tissues and tumors.

Example 4

Synthesis of Triazene Precursor

A triazine precursor of compounds of the present invention was prepared as shown below.

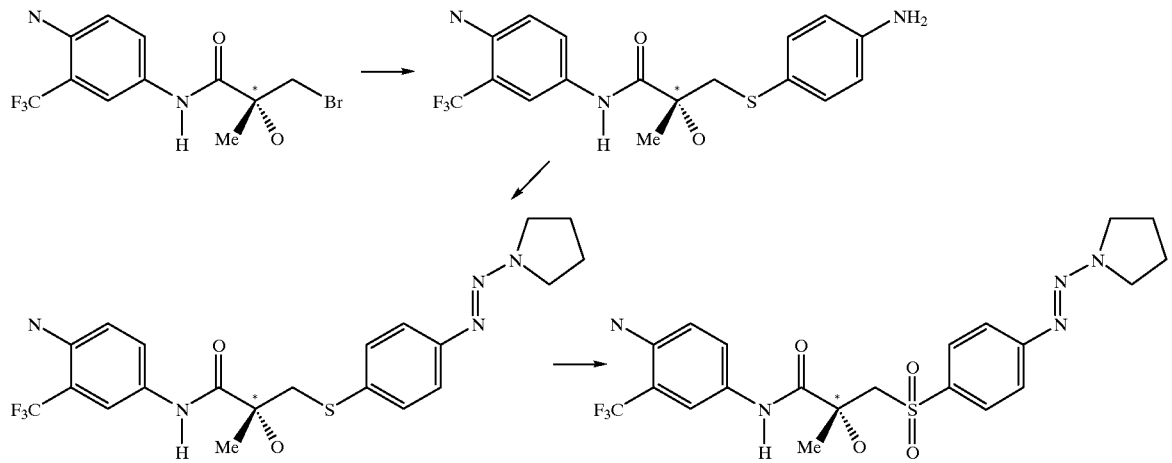

Synthesis of the triazine precursor was performed in three steps, starting with bromoanilide (prepared as described in Example 2). The first step involved coupling of commercially available 4-aminothiophenol, ionized by one equivalent of sodium hydride, with bromoanilide in THF at room temperature to form an amino-Bicalutamide analog. Because of the electron-donating character of the amino group, ionization of 4-aminothiophenol took approximately 24 hours (unlike ionization reactions of other previously described thiophenols, which took less then 1 hour). The use of one equivalent of sodium hydride allowed any side reaction of bromoanilides with the amino-portion of 4-aminothiophenol to be avoided. Preparation of the triazene compound was carried out according to general procedure described by Counsell (Van Dort et al., "Radioiodinated P-Iodoclonidine: A High-Affinity Probe For The Alpha 2-Adrenergic Receptor," J. Med. Chem., 30:1241–44 (1987)). A sample of amino-Bicalutamide analog was placed into an aqueous solution of sulfuric acid in a beaker, to which a pre-cooled aqueous solution of $NaNO_2$ was added dropwise. The final green solution was filtered, and pyrrolidine was added dropwise to this solution at ice-bath temperature. The yellow solid product of the reaction was filtered, dried, and used for the next step without further purification. It was oxidized to the final triazene precursor by m-chloroperbenzoic acid in methylene chloride at room temperature.

Example 5

Radiochemical Synthesis and Purification of Iodinated Compounds from the Triazene Precursor Synthesis and initial purification of a radiolabeled iodo-compound of the present invention from the triazene precursor was carried out as shown below.

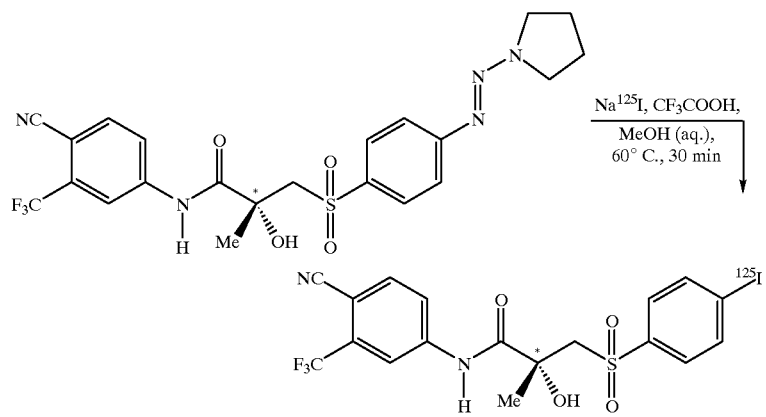

Figure 2:
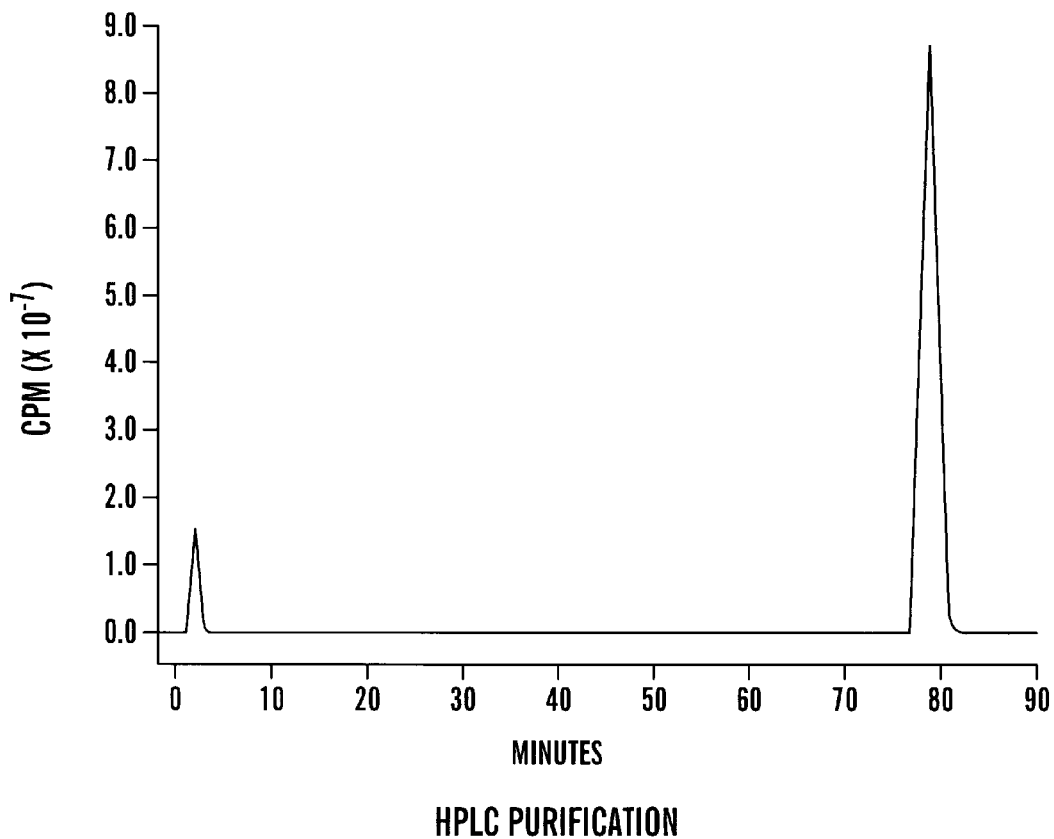
FIG. 2 is a graph that shows the HPLC purification of the R-isomer of an $^{125}$Iodo-labeled compound of the present invention.

A methanolic reaction mixture containing trifluoroacetic acid, a 100-fold molar excess of the triazene precursor and sodium iodide ($^{125}I$) were heated at 60° C. for 30 minutes and then neutralized with aqueous sodium hydroxide. The reaction mixture was cooled to room temperature, and immediately mixed with 5 ml of chloroform. The chloroform extract was evaporated to dryness under a gentle stream of nitrogen, re-dissolved in mobile phase, and then immediately injected to the HPLC system. Separation was achieved using 35% aqueous acetonitrile as a mobile phase and a reversed phase column (Novapak C18, Waters Chromatograph, Milford, Mass.). As shown in FIG. 2, the majority (>88%) of $^{125}I$-labeled product eluted with a retention time of 79 minutes, corresponding exactly with the retention time of previously injected non-radiolabeled compound standards. The determination of specific activity and radiochemical purity of the final product is being investigated. The reactions using $^{123}$I sodium iodide were also successful.

Example 6

Synthesis of Trimethyltin Precursor

A trimethyltin precursor of compounds of the present invention was prepared as below.

syringe to a centrifuged (3000 rpm, 2 minutes) solution of radioactive sodium iodide (Na$^{125}$I, 1 mCi, Amersham Corporation, Arlington Heights, Ill.) in P15 microvial. Aqueous solution of Chloramine-T (Aldrich Chemical Co., Milwaukee, Ill., 50 μl with approximate concentration 2 mg/ml) was added by syringe followed by 50 μl of 0.1N aqueous hydrochloric acid solution. The reaction mixture was vortexed for 1 minute, and left at room temperature for 30 minutes. After that, 100 μl of aqueous Na$_2$S$_2$O$_5$ solution (approximate concentration 20 mg/ml) was injected into the

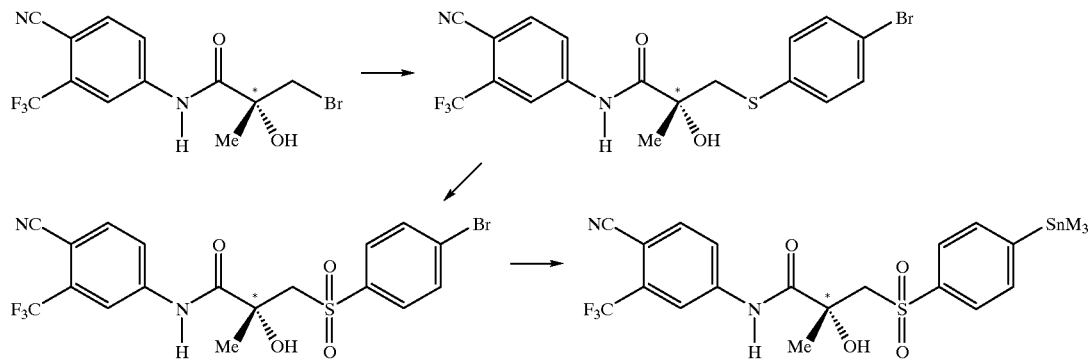

Synthesis of trimethyltin precursor was performed in three steps, starting with bromoanilide (prepared as described in Example 2). The first step involved coupling of commercially available 4-bromothiophenol, ionized by sodium hydride, with bromoanilide in THF at room temperature. The product of the reaction was oxidized to the bromo-analog of Bicalutamide by peracetic acid in acetone or ethylacetate at room temperature. Reflux of the formed product in toluene with hexamethylditin Sn$_2$Me$_6$ and Pd(PPh$_3$)$_4$ in the presence of triethylamine for 1 hour gave rise to the trimethyltin precursor, which was purified by flash chromatography.

Example 7

Radiochemical Synthesis and Purification of Lodinated Compounds from the Trimethyltin Precursor Synthesis and initial purification of a radiolabeled iodo-compound of the present invention from the trimethyltin precursor was carried out as shown below.

reaction mixture. The reaction mixture was vortexed, and immediately extracted 3 times with 5 ml chloroform. Chloroform layers were combined together and dried in a flow of nitrogen. The final crude product was re-suspened into 45% aqueous acetonitrile, and purified by injection into an HPLC system consisting of a Novapak C$_{18}$ reversed phase column and an on line UV detector. Fractions were collected for 1 minute periods from the HPLC system, and the radioactivity in each fraction was counted in a liquid scintillation counter. The total yield of the radiolabeled R-iodo-compound was 95% with specific activity 940 Ci/mmol. The trimethyltin precursor is preferred over the triazene precursor because of the higher yield.

Example 8

Purification of Compounds from Reaction Mixtures

Compounds of the present invention were purified from crude reaction mixture using either normal or reversed-phase HPLC columns.

For example, the Compound formed in Example 5 is easily and quickly separated from its triazene precursor

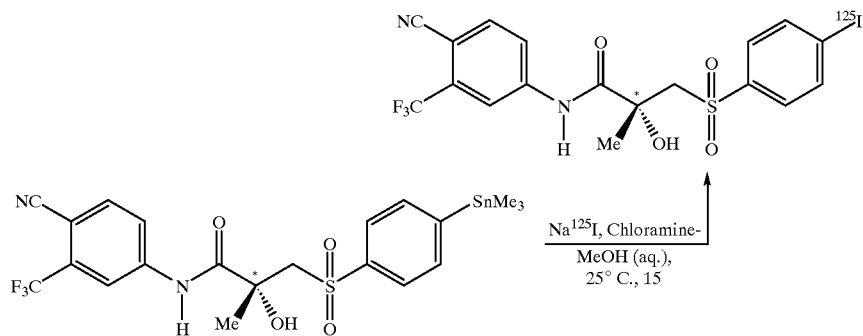

A methanolic solution of trimethyltin precursor (100 μl with approximate concentration 1 mg/ml) was added by using an aqueous mobile phase containing 35% acetonitrile and 25 mM phosphate buffer, pH 7.0, and a Novapak C18 reversed-phase column (Waters Chromatography, Milford, Mass.) with retention times of 82 and 69 minutes, respectively. HPLC eluent was collected and fractions containing R-iodo-compound were extracted with 5 ml of chloroform to yield the pure compound (>99% chemical purity). Spiked standards showed that greater than 90% of the target compound could be recovered from reaction mixtures using these procedures.

Normal phase chromatographic methods are also suitable for purification of compounds of the present invention. Normal phase chromatography (μPorasil, 10 μm particle size columns; Waters Chromatography) allows for more rapid separation of the reaction mixture (i.e., the R-iodo-compound of Example 5 elutes at 28 minutes in an organic mobile phase consisting of 20% hexane in methylene chloride while the triazene precursor is retained for 60 minutes) and avoids extraction of the compounds from the aqueous mobile phase during reversed phase chromatography.

For each new ligand, the retention times of the target and precursor compounds must first be determined in preliminary experiments by monitoring the UV absorbance of non-radiolabeled standards. Radiolabeled target compounds are then collected in appropriate HPLC fractions, extracted into chloroform, and evaporated to dryness under nitrogen. Specific activity is then determined using quantitative HPLC. Calibration curves are generated by injection of known standards, and the mass of injected sample determined by comparison of its UV absorbing peak to the calibration curve. The activity in the eluted peak is determined by liquid scintillation counting or gamma counting. Radiochemical purity is determined using HPLC or TLC analyses. TLC separation methods are also suitable. In this instance, two-phase solvent systems are used to separate each radioligand of interest from the precursor (e.g., triazene precursor) using commercially available 5×20 cm silica plates. Previous studies have shown that bicalutamide can be separated from its polar metabolites using mixtures of ethyl acetate/acetic acid (97/3 v/v) as the solvent system (Boyle, G. W., et al., "Metabolism of Casodex in Laboratory Animals," *Xenobiotica* 23:781–798 (1993)). To the extent they have not already been identified, TLC methods based on Boyle et al. ("Metabolism of Casodex in Laboratory Animals," *Xenobiotica* 23:781–798 (1993) will allow for adaptation to new compounds. Analyses are then performed on a radio-TLC scanner or by scraping and gamma/beta counting. Radiochemical purity is calculated as (CPM in the peak of interest) divided by total radioactivity observed during chromatography.

Example 9

Tissue Distribution of $^{125}$I-Labeled R-Iodo-Bicalutamide Following Administration Tissue distribution studies were performed in castrated, male Copenhagen rats. A cannula was placed in the jugular vein of the rat at the time of castration. A bolus dose of 100 μCi of the radiolabeled R-iodo-compound (prepared in Examples 5 and 7), in 50% ethanol in saline, was injected via the jugular vein. Rats (n=3 at each time point) were sacrificed at 0.5, 1, 2, 3, 5, 7, and 10 day time points. Organs were harvested, blotted dry, and stored at −20° C. until analysis. Plasma, liver, kidney, lungs, heart, muscle, fat, prostate, seminal vesicle, epididymis, pancreas, spleen, brain, and thyroid were collected. Organs were weighed, minced, and homogenized in a Pro 200 homogenizer (Pro Scientific, Monroe, Conn.). Homogenates were spiked with an internal standard, R-bicalutamide, and extracted with ethyl acetate, followed by centrifugation for 20 minutes at 3000. An aliquot of supernatant was dried under nitrogen, and the residue re-suspended in a mixture of 50% ethanol and n-hexane and then vortexed. Next the tubes were centrifuged at 3000 rpm for 5 minutes, and the supernatant was discarded. Sodium phosphate buffer (25 mM, pH 7.0) and chloroform were added to the tubes, followed by vortexing. The tubes were centrifuged at 3000 rpm for 5 minutes, and the supernatant discarded. The chloroform layer was dried under nitrogen, and the residue re-suspended in mobile phase. An aliquot (140 μL) was injected into an HPLC system, which consisted of a Waters Model 510 solvent pump (Waters, Milford, Mass.), a WISP 710B auto-injector (Waters), a Waters Model 480 UV detector, and a Radiomatic FLO-ONE/∃ radioactive flow detector (Packard Instrument Company, Downers Grove, Ill.). Standard curves for the quantitation of the radiolabeled R-iodo-compound were constructed using blank liver and lung tissue homogenates. Total radioactivity in homogenates was quantitated in a Beckman LS6800 liquid scintillation counter.

Figure 3:
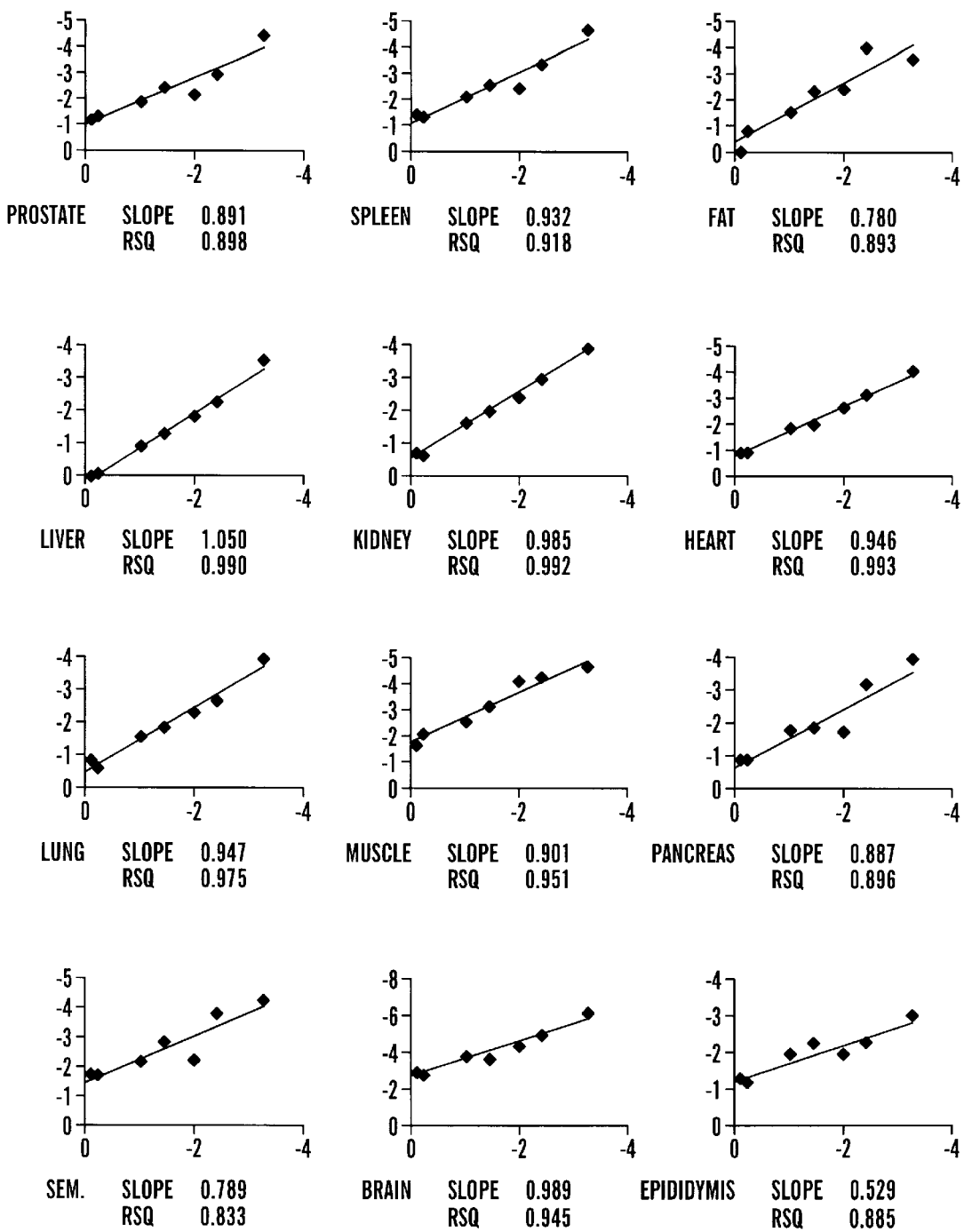
FIG. 3 is series of graphs that show the retention of the R-isomer of an $^{125}$Iodo-labeled compound of the present invention in the tissues of rats administered an intravenous dose.

Distribution of the radiolabeled R-iodo-compound into organs was proportional to blood flow to each organ. Concentrations in liver were very similar to plasma concentrations over the entire range of time points. Distribution into lungs, kidney, and heart, which have similar blood flows, was high. Distribution into prostate, seminal vesicle, and epididymis was lower due to lower blood flow to these organs. Concentrations in liver, lung, kidney, heart, muscle, spleen and brain declined in parallel with plasma concentrations, indicating the absence of selective retention in these tissues. Concentration-time profiles in prostate, seminal vesicle and epididymis, which are rich in AR, showed a plateau at 3 to 5 days, suggesting selective retention in these tissues. This was further confirmed using log tissue concentration versus log plasma concentration plots, as shown in FIG. 3. While other organs showed a slope close to 1.0, slopes for prostate, seminal vesicle and epididymis were significantly lower, indicating that concentrations in these tissues did not decline in parallel with plasma concentration. Tissue concentration to plasma concentration ratios were similar over the entire time range for all organs except prostate, seminal vesicle and epididymis. For the prostate, the ratio increased steadily up to 5 days, when it exceeded the ratio in all other organs except the liver. These data indicate that the tissue distribution of non-steroidal androgen receptor ligands is favorable to permit non-invasive imaging of androgen receptor-positive tissues, including the prostate and associated tumors.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A radiolabeled non-steroidal compound having the formula:

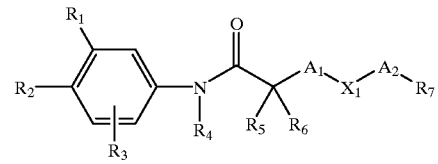

where $R_1$, $R_2$ and $R_3$, are the same or different and are a radioactive or nonradioatctive halogen, a nitro, a cyano, a carbamoyl, a hydrogen, a perfluoroalkyl, a haloalkylamido, an isothiocyanate, an azide, a diazocarbonyl, a substituted oxirane, or a β-chloroethylamine;

$R_4$ is a hydrogen, an alkyl, or is joined to $R_5$;

$R_5$ is a radioactive or nonradioactive halogen, a hydrogen, a hydroxy, an alkyl, a haloalkyl, an alkoxy, an acyloxy, an amino, an alkylamino, a thio, a thioalkyl, or is joined to $R_4$ to form a five-membered ring optionally containing a hetero-atom as a ring member;

$R_6$ is a hydrogen, an alkyl, a halogen, or a haloalkyl;

$A_1$ and $A_2$ are the same or different, and each is a direct link or an alkylene;

$X_1$ is an oxygen, a sulfur, a sulphinyl, a sulphonyl, an alkylimino, or alkylene;

$R_7$ is a radioactive or nonradioactive halogen, a hydrogen, an aloxy, a haloalkoxy, an acyloxy, a haloacyloxy, an aryloxy, a thioalkyl, a thioraryl, an alkylsulphinyl, an arylsulphinyl, an alkylsulphonyl, an arylsulphonyl, an amino, an alkylimino, an alkylamido group, a radioactive or nonradioactive, haloalkylamido group, a phenyl optionally substituted with a radioactive or nonradioactive halogen, a nitro group, an alkyl, a radioactive or nonradioactive haloalkyl, a cyano, a hydroxyl, a caboxyl group, an amino, an alkylamino group, a dialkylamino group, a bisalkylamino group, a radioactive or nonradiactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradiactive bis(haloacyl)imido group, or a radioactive or nonradioactive alkyhaloacylamido group.

2. A radiolabeled non-steroidal compound according to claim 1, wherein the compound is an androgen receptor ligand.

3. A radiolabeled non-steroidal compound according to claim 2, wherein the compound is an androgen receptor antagonist.

4. A radiolabeled non-steroidal compound according to claim 2, wherein the compound is an androgen receptor agonist.

5. A radiolabeled non-steroidal compound according to claim 1, wherein the compound is a substantially pure R-enantiomer.

6. A radiolabeled non-steroidal compound according to claim 1, wherein $R_1$ is $CF_3$, $R_2$ is CN or $NO_2$, $R_3$ is H, $R_4$ is H and $R_5$ is OH, or $R_4$ and $R_5$ are joined together ad SCO, $R_6$ is $CH_3$ or $CF_3$, $A_1$ is an alkylene or a direct link, $A_2$ is a direct link, $X_1$ is $CH_2$, S, or $SO_2$, and $R_7$ is a radioactive or nonradioactive halogen, or a phenyl optionally substituted with a radioactive or nonradioactive halogen, a nitro group, an alkyl, a radioactive or nonradioactive haloalkyl, a cyano, a hydroxyl, a carboxyl group, an amino, an alkylamino group, a dialkylamino group, a bisalkylamino group, a radioactive or nonradioactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradioactive bis(haloacyl)imido group, or a radioactive or nonradioactive alkylhaloacylamido group.

7. A radiolabeled non-steroidal compound according to claim 6, wherein $R_2$ is CN or $NO_2$, $R_4$ is H, $R_5$ is OH, $A_1$ is a direct link, $X_1$ is $CH_2$, and $R_7$ is a radioactive halogen.

8. A radiolabeled non-steroidal compound according to claim 6, wherein $R_2$ is CN, $R_4$ is H, $R_5$ is OH, $A_1$ is an alkylene, $X_1$ is S or $SO_2$, and $R_7$ is a phenyl group substituted with a radioactive halogen.

9. A radiolabeled non-steroidal compound according to claim 6, wherein $R_2$ is CN, $R_4$ and $R_5$ are joined together as SCO, $A_1$ is an alkylene, $X_1$ is S or $SO_2$, and $R_7$ is a phenyl group substituted with a radioactive halogen.

10. A composition comprising:

a radiolabeled non-steriodal compound and a pharmaceutically acceptable carrier;

wherein the radiolabeled non-steroidal compound has the formula:

where $R_1$, $R_2$ and $R_3$, are the same or different and are a radioactive or nonradioactive halogen, a nitro, a cyano, a carbamoyl, a hydrogen, a perfluoroalkyl, a haloalkylamido, an isothiocyanate, an azide, a diazocarbonyl, a substituted oxirane, or a β-chloroethylamine;

$R_4$ is a hydrogen, an alkyl, or is joined to $R_5$;

$R_5$ is radioactive or nonradioactive halogen, a hydrogen, a hydroxy, an alkyl, a haloalkyl, an alkoxy, an acyloxy, an amino, an alkylamino, a thio, a thioalkyl, or is joined to $R_4$ to form a five-membered ring optionally containing a hetero-atom as a ring member;

$R_6$ is a hydrogen, an alkyl, a halogen, or a haloalkyl;

$A_1$ and $A_2$ are the same or different, and each is a direct link or an alkylene;

$X_1$ is an oxygen, a sulfur, a sulphinyl, a sulphonyl, an alkylimino, or alkylene;

47

$R_7$ is a radioactive or nonradioactive halogen, a hydrogen, an alkoxy, a haloalkoxy, an acyloxy, a haloacyloxy, an aryloxy, a thioalkyl, a thioaryl, an alkylsulphinyl, an arylsulphinyl, an alkylsulphonyl, an arylsulphonyl, an amino, an alkylimino, an alkylamido group, a radioactive or nonradioactive haloakylamido group, a phenyl optionally substituted with a radioactive or nonradioactive halogen, a nitro group, an alkyl, a radioactive or nonradioactive haloalkyl, a cyano, a hydroxyl, a carboxyl group, an amino, an alkylamino group, a dialkylamino group, a bisalkylamino group, a radioactive or nonradioactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradioactive bis(haloacyl) imido group, or a radioactive or nonradioactive alkylhaloacylamido group.

11. A composition according to claim 10, wherein the compound is an androgen receptor ligand.

12. A composition according to claim 11, wherein the compound is an androgen receptor antagonist.

13. A composition according to claim 11, wherein the compound is an androgen receptor agonist.

14. A composition according to claim 10, wherein the compound is a substantially pure R-enantiomer.

15. A composition according to claim 10, wherein $R_1$ is $CF_3$, $R_2$ is CN or $NO_2$, $R_3$ is H, $R_4$ is H and $R_5$ is OH, or $R_4$ and $R_5$ are joined together as SCO, $R_6$ is $CH_3$ or $CF_3$, $A_1$ is an alkylene or a direct link, $A_2$ is a direct link, $X_1$ is $CH_2$, or S, or $SO_2$, and $R_7$ is radioactive or nonradioactive halogen, or a phenyl optionally substituted with a radioactive or nonradioactive halogen, a nitro group, an alkyl, a radioactive or nonradioactive haloalkyl, a cyano, a hdyroxyl, a carboxyl group, an amino, an alkylamino group, a dialkylamino group, a bisalkylamino group, a radioactive or nonradioactive haloalkylamino group, a radioactive or nonradioactive dihaloalkylamino group, a radioactive or nonradioactive bishalaoalkylamino group, an acyalmido group, a diacylamido group, an alkylacylamido group, a radioactive or nonradioactive haloacylamido group, a radioactive or nonradioactive bis(haloacyl)imido group, or a radioactive or nonradioactive alkylhaloacylamido group.

16. A method of imaging for prostate cancer or other androgen receptor containing tissues in a patient comprising:

contacting an androgen receptor with a radiolabeled non-steroidal compound under conditions effective to bind the radiolabeled non steroidal compound to the androgen receptor; and detecting the presence of any radiolabeled non-steroidal compound bound to the androgen receptor;

wherein the radiolabeled non-steroidal compound has the formula;

48

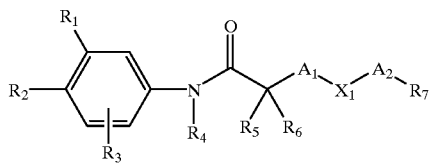

where $R_1$, $R_2$ and $R_3$, are the same or different and are a radioactive or nonradioactive halogen, a nitro, a cyano, a carbamoyl, a hydrogen, a perfluoroalkyl, a haloalkylamido, an isothiocyanate, an azide, a diazocarbonyl, a substituted oxirane, or a β-chloroethylamine;

$R_4$ is a hydrogen, an alkyl, or is joined to $R_5$;

$R_5$ is a radioactive or nonradioactive halogen, a hydrogen, a hydroxy, an alkyl a haloalkyl, an alkoxy, an acyloxy, an amino, an alkylamino, a thio, a thioalkyl, or is joined to $R_4$ to form a five-membered ring optionally containing a hetero-atom as a ring member;

$R_6$ is a hydrogen, an alkyl, a halogen, or a haloalkyl;

$A_1$ and $A_2$ are the same or different, and each is a direct link or an alkylene;

$X_1$ is an oxygen, a sulfur, a sulphinyl, a sulphonyl, an alkylimino, or alkylene;

$R_7$ is a radioactive or nonradioactive halogen, a hydrogen, an alkoxy, a haloalkoxy, an acyloxy, a haloacyloxy, an aryloxy, a thioalkyl, a thioaryl, an alkysulphinyl, an arylsulphinyl, an alkysulphonyl, an arylsulphonyl, an amino, an alkylimino, an alkylamido group, a radioactive or nonradioactive haloalkylamido group, or a phenyl optionally substituted with a radioactive or nonradioactive halogen, a nitro group, an alkyl, a radioactive or nonradioactive haolalkyl, a cyano, a hydroxyl, a carboxyl, group, an amino, an alkylamino group, a dialkylamino group, a bisalkylamino group, a radioactive or nonradioactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradioactive bis (haloacyl)imido group, or a radioactive or nonradioactive alkyhaloacylamido group.

17. A method according to claim 16, wherein $R_1$ is $CF_3$, $R_2$ is CN or $NO_2$, $R_3$ is H, $R_4$ is H and $R_5$ is OH, or $R_4$ and $R_5$ are joined together as SCO, $R_6$ is $CH_3$ or $CF_3$, $A_1$ is an alkylene or a direct link, $A_2$ is a direct link, $X_1$ is $CH_2$, S, or $SO_2$, and $R_7$ is a radioactive or nonradioactive halogen, or a phenyl optionally substituted with a radioactive or nonradioactive halogen, a nitro group, an alkyl, a radioactive or nonradioactive haloalkyl, a cyano, a hydroxyl, a carboxylic group, an amino, an alkylamino group, a dialkylamino group, a bisalkylamino group, a radioactive or nonradioactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradioactive bis(haloacyl)imido group, or a radioactive or nonradioactive alkylhaloacylamido group.

18. A method of producing a radiolabeled non-steroidal compound comprising:

providing a precursor compound having the formula

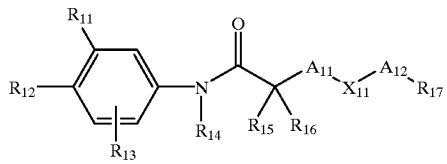

wherein $R_{11}$, $R_{12}$ and $R_{13}$, are the same or different, and each is a hydrogen, a halogen, a nitro, a cyano, a carbamoyl, a perfluoroalkyl, a haloalkylamido, an isothiocyanate, an azide, a diazocarbonyl, a substituted oxirane, a β-chloroethylamine, a diazonium salt, a triazene group, a tertiary alklyl group, an oxy group, an alkoxy group, a stannoalkyl group, a stannoaryl group, an unsubstituted or substituted boronic acid, an alkyl silane group, a pentaflourosilicate group, an alkylgermano group, a halomercury group, a trifluoroacetylthallate group, or a thallium difluoride group, $R_{14}$ is a hydrogen, an alkyl, or is joined to $R_{15}$, $R_{15}$ is a hydrogen, a hydroxy, an alkyl, a haloalkyl, an alkoxy, an acyloxy, an amino, an alkylamino, a thiol, a thioalkyl, a halogen, or is joined to $R_{14}$ or $X_{11}$;

$R_{16}$ is a hydrogen, an alkyl, a halogen, or a haloalkyl, $A_{11}$ and $A_{12}$ are the same or different, and each is a direct link or alkylene, $X_{11}$ is a halogen, an oxygen, a sulfur, a sulphinyl, a sulfonyl, an amino, an alkylimino, an alkylene, or is joined to $R_{15}$ directly, through an oxirane ring, through an $SO_2$ group, or through an SO group, and $R_{17}$ is an aryl ring, substituted at different positions with a hydrogen, a halogen, a diazonium salt, a triazene group, a tertiary alkyl amino group, a nitro group, an oxy group, an alkoxy group, an amino group, an alkylamino group, a stannoalkyl group, a stannoaryl group, an unsubstituted or a substituted boronic acid, an alkyl silane group, a pentafluorosilicate group, an alkylgermano group, a halomercury group, a trifluoroacetyl thallate group, or a thallium difluoride group;

providing a radioactive compound; and reacting the precursor compound and the radioactive compound under conditions effective to produce a radiolabeled non-steroidal compound having the formula:

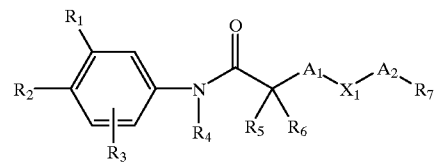

where $R_1$, $R_2$ and $R_3$, are the same or different and are a radioactive or nonradioactive halogen, a nitro, a cyano, a carbamoyl, a hydrogen, a perfluoroalkyl, a haloalkylamido, an isothiocyanate, an azide, a diazocarbonyl, a substituted oxirane, or a βchloroethylamine, $R_4$ is a hydrogen, an alkyl, or is joined to $R_5$, $R_5$ is a radioactive or nonradioactive halogen, a hydrogen, a hydroxy, an alkyl, a haloalkyl, an alkoxy, an acyloxy, an amino, an alkylamino, a thio, a thioalkyl, or is joined to $R_4$ to form a five membered ring optionally containing a hetero-atom as a ring member, $R_6$ is a hydrogen, an alkyl, a halogen, or a haloalkyl, $A_1$ and $A_2$ are the same or different, and each is a direct link or an alkylene, $X_1$ is an oxygen, a sulfur, a sulphinyl, a sulphonyl, an alkylimino, or alkylene, and $R_7$ is a radioactive or nonradioactive halogen, a hydrogen, an alkoxy, a haloalkoxy, an acyloxy, a haloacyloxy, an aryloxy, a thioalkyl, a thioraryl, an alkysulphinyl, an arysulphinyl, an alkylsulphonyl, an arylsulphonyl, an amino, an alkylimino, an alkylamido group, a radioactive or nonradioactive haloalkylamido group, a phenyl optionally substituted with a radioactive or nonradioactive halogen, a nitro group, an alkyl, a radioactive or nonradioactive haloalkyl, a cyano, a hydroxyl, a carboxyl group, an amino, an alkylamino group, a dialkylamino group, a bisalkylamino group, a radioactive or nonradioactive haloalkylamino group, a radioactive or nonradioactive dihaloalkylamino group, a radioactive or nonradioactive bishaloalkylamino group, an acylamido group, a diacylamido group, an alkylacylamido group, a radioactive or nonradioactive haloacylamido group, a radioactive or nonradioactive bis(haloacyl)imido group, or a radioactive or nonradioactive alkylhaloacylamido group.

19. A method according to claim 18, wherein $R_7$ of the precursor compound is a phenyl substituted with a triazene group or a stannoalkyl or a stannoaryl group.

* * * * *